United States Patent
Fleury et al.

(10) Patent No.: US 10,172,834 B2
(45) Date of Patent: *Jan. 8, 2019

(54) (2R,4R)-5-(5'-CHLORO-2'-FLUOROBIPHENYL-4-YL)-2-HYDROXY-4-[(5-METHYLOXAZOLE-2-CARBONYL)AMINO]PENTANOIC ACID

(71) Applicant: THERAVANCE BIOPHARMA R&D IP, LLC, South San Francisco, CA (US)

(72) Inventors: Melissa Fleury, Brisbane, CA (US); Adam D. Hughes, Half Moon Bay, CA (US); Anne-Marie Beausoleil, Redwood City, CA (US); Erik Fenster, San Bruno, CA (US); Venkat R. Thalladi, Foster City, CA (US); Miroslav Rapta, San Carlos, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,799

(22) Filed: Dec. 14, 2017

(65) Prior Publication Data

US 2018/0228774 A1    Aug. 16, 2018

Related U.S. Application Data

(63) Continuation of application No. 15/357,269, filed on Nov. 21, 2016, now Pat. No. 9,872,855, which is a continuation of application No. 15/042,391, filed on Feb. 12, 2016, now Pat. No. 9,533,962.

(60) Provisional application No. 62/118,067, filed on Feb. 19, 2015.

(51) Int. Cl.

| C07D 263/34 | (2006.01) |
| A61K 31/421 | (2006.01) |
| A61K 9/48 | (2006.01) |
| A61K 47/12 | (2006.01) |
| C30B 7/14 | (2006.01) |
| C30B 29/54 | (2006.01) |
| A61K 45/06 | (2006.01) |

(52) U.S. Cl.
CPC .......... *A61K 31/421* (2013.01); *A61K 9/4816* (2013.01); *A61K 9/4825* (2013.01); *A61K 45/06* (2013.01); *A61K 47/12* (2013.01); *C07D 263/34* (2013.01); *C30B 7/14* (2013.01); *C30B 29/54* (2013.01); *C07B 2200/13* (2013.01)

(58) Field of Classification Search
None
See application file for complete search history.

(56) References Cited

U.S. PATENT DOCUMENTS

| 4,189,604 A | 2/1980 | Umezawa et al. |
| 4,206,232 A | 6/1980 | Ondetti et al. |
| 4,374,829 A | 2/1983 | Harris et al. |
| 4,513,009 A | 4/1985 | Roques et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |

(Continued)

FOREIGN PATENT DOCUMENTS

WO    2011/088797 A1    7/2011

OTHER PUBLICATIONS

Ksander et al., "Dicarboxylic acid dipeptide neutral endopeptidase inhibitors", Journal of Medicinal Chemistry, 38(10): 1689-1700 (1995).
Misawa et al., "Structure-based design of dipeptide derivatives for the human neutral endopeptidase", BioOrganic & Medicinal Chemistry, 19: 5935-5947 (2011).
PCT International Search Report for PCT/US2011/064829 dated Feb. 17, 2012.
PCT International Search Report for PCT/US2016/017699 dated Apr. 21, 2016.

*Primary Examiner* — Michael Barker
(74) *Attorney, Agent, or Firm* — Jeffrey A. Hagenah; Wendy Petka

(57) ABSTRACT

In one aspect, the invention relates to a compound of the structure:

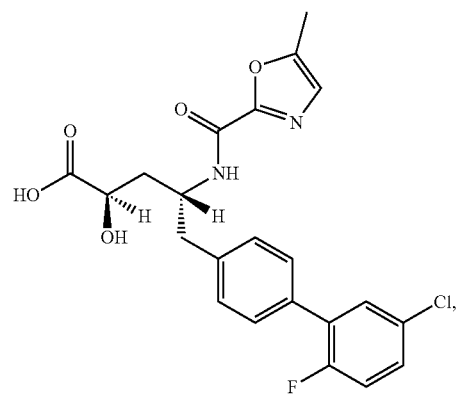

(1)

or a pharmaceutically acceptable salt thereof, and a crystalline form of this compound, having neprilysin inhibition activity. In another aspect, the invention relates to pharmaceutical compositions comprising this compound; methods of using this compound; and processes for preparing this compound.

3 Claims, 3 Drawing Sheets

(56) References Cited

U.S. PATENT DOCUMENTS

| | | |
|---|---|---|
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 9/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,686,184 B2 | 4/2014 | Fleury et al. |
| 8,691,868 B2 | 4/2014 | Hughes et al. |
| 8,846,913 B2 | 9/2014 | Fleury et al. |
| 8,871,792 B2 | 10/2014 | Hughes et al. |
| 9,045,443 B2 | 6/2015 | Mammen et al. |
| 9,108,934 B2 | 8/2015 | Hughes et al. |
| 9,120,747 B2 | 9/2015 | Gendron et al. |
| 9,126,956 B2 | 9/2015 | Fleury et al. |
| 9,533,962 B2 | 1/2017 | Fleury et al. |
| 9,872,855 B2 * | 1/2018 | Fleury .................. A61K 45/06 |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0157383 A1 | 6/2012 | Gendron et al. |
| 2012/0309724 A1 | 12/2012 | Fleury et al. |

\* cited by examiner

(2R,4R)-5-(5'-CHLORO-2'-FLUOROBIPHENYL-4-YL)-2-HYDROXY-4-[(5-METHYLOXAZOLE-2-CARBONYL)AMINO]PENTANOIC ACID

CROSS-REFERENCE TO RELATED APPLICATION

This application is a continuation of U.S. application Ser. No. 15/357,269, filed on Nov. 21, 2016, now allowed; which is a continuation of U.S. application Ser. No. 15/042,391, filed on Feb. 12, 2016, now patented (U.S. Pat. No. 9,533, 962 B2); which application claims the benefit of U.S. Provisional Application No. 62/118,067, filed on Feb. 19, 2015; the entire disclosures of which are incorporated herein by reference.

BACKGROUND OF THE INVENTION

Field of the Invention

The present invention relates to a novel compound and a crystalline form thereof having neprilysin-inhibition activity. The invention also relates to pharmaceutical compositions comprising compound, processes for preparing compound, and methods of using compound to treat diseases such as hypertension, heart failure, and renal disease.

State of the Art

Neprilysin (neutral endopeptidase, EC 3.4.24.11) (NEP), is an endothelial membrane bound $Zn^{2+}$ metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) *Exp. Opin. Ther. Patents* 9(12): 1665-1677.

Numerous NEP inhibitors are described in U.S. Pat. No. 8,263,629 to Coppola et al and U.S. Pat. No. 8,586,536 to Gendron et al. Many of these compounds have one or more desirable properties. In spite of these compounds however, there remains a need for a potent NEP inhibitor that has high oral bioavailability and low clearance across all species tested. This invention is directed to that need.

Additionally, to effectively use a NEP inhibitor compound as a therapeutic agent, it would be desirable to have a solid-state form that can be readily manufactured and that has acceptable chemical and physical stability. For example, it would be highly desirable to have a physical form that is thermally stable at reasonably high temperature, thereby facilitating processing and storage of the material. Crystalline solids are generally preferred over amorphous forms, for enhancing purity and stability of the manufactured product. However, the formation of crystalline forms of organic compounds is highly unpredictable. No reliable methods exist for predicting which, if any, form of an organic compound will be crystalline. Moreover, no methods exist for predicting which, if any, crystalline form will have the physically properties desired for use as pharmaceutical agents. Accordingly, a need exists for a stable, crystalline form which has a reasonably high melting point.

SUMMARY OF THE INVENTION

The present invention provides a novel Compound (1) that has been found to possess neprilysin (NEP) enzyme inhibition activity. Accordingly, this compound is expected to be useful and advantageous as a therapeutic agent for treating conditions such as hypertension, pulmonary hypertension, heart failure and renal disease.

One aspect of the invention relates to (2R,4R)-5-(5'-chloro-2'-fluorobiphenyl-4-yl)-2-hydroxy-4-[(5-methyl-oxazole-2-carbonyl)amino]pentanoic acid (1):

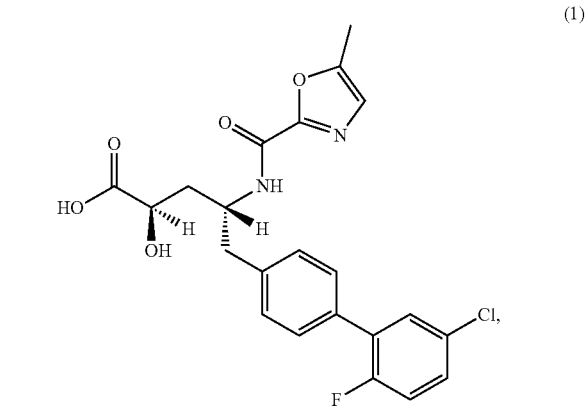 [SMILES: Cc1cnc(C(=O)N[C@H](Cc2ccc(-c3cc(Cl)ccc3F)cc2)C[C@@H](O)C(=O)O)o1]

(1)

or a pharmaceutically acceptable salt thereof Another aspect of the invention relates to a crystalline form of Compound 1. In one embodiment, the crystalline form (1') is non-solvated.

Another aspect of the invention relates to pharmaceutical compositions comprising one or more pharmaceutically acceptable carriers and Compound 1 or a crystalline form thereof. Such compositions may optionally contain other therapeutic agents, including but not limited to, an $AT_1$ receptor antagonist, an angiotensin-converting enzyme inhibitor, a phosphodiesterase (PDE) inhibitor, a renin inhibitor, a diuretic, or combinations thereof.

Compound 1 of the invention possesses NEP enzyme inhibition activity, and is therefore expected to be useful as a therapeutic agent for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of Compound 1. Another aspect of the invention relates to a method of treating hypertension, pulmonary hypertension, heart failure, or renal disease, comprising administering to a subject a therapeutically effective amount of Compound 1. Still another aspect of the invention relates to a method for inhibiting a NEP enzyme in a subject comprising administering to the subject, a NEP enzyme-inhibiting amount of Compound 1.

Since Compound 1 of the invention possesses NEP inhibition activity, it is also useful as a research tool. Accordingly, one aspect of the invention relates to a method of using Compound 1 of the invention as a research tool, the method comprising conducting a biological assay using Compound 1. Compound 1 can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with Compound 1 to provide a second assay value; wherein step (a) is conducted either before, after or concurrently with step (b); and (c) comparing the first assay value from step (a) with the second assay value from step (b). Exemplary biological assays include a NEP enzyme inhibition assay. Still another aspect of the invention relates to a method of studying a biological system or sample comprising a NEP enzyme, the method comprising: (a) contacting the biological system or sample with Compound 1; and (b) determining the effects caused by Compound 1 on the biological system or sample.

Yet another aspect of the invention relates to processes useful for preparing Compound 1 or a crystalline form thereof.

Yet another aspect of the invention relates to the use of Compound 1 or a crystalline form thereof for the manufacture of a medicament, especially for the manufacture of a medicament useful for treating hypertension, heart failure, or renal disease. Another aspect of the invention relates to use of Compound 1 or crystalline form thereof for inhibiting a NEP enzyme in a subject. Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
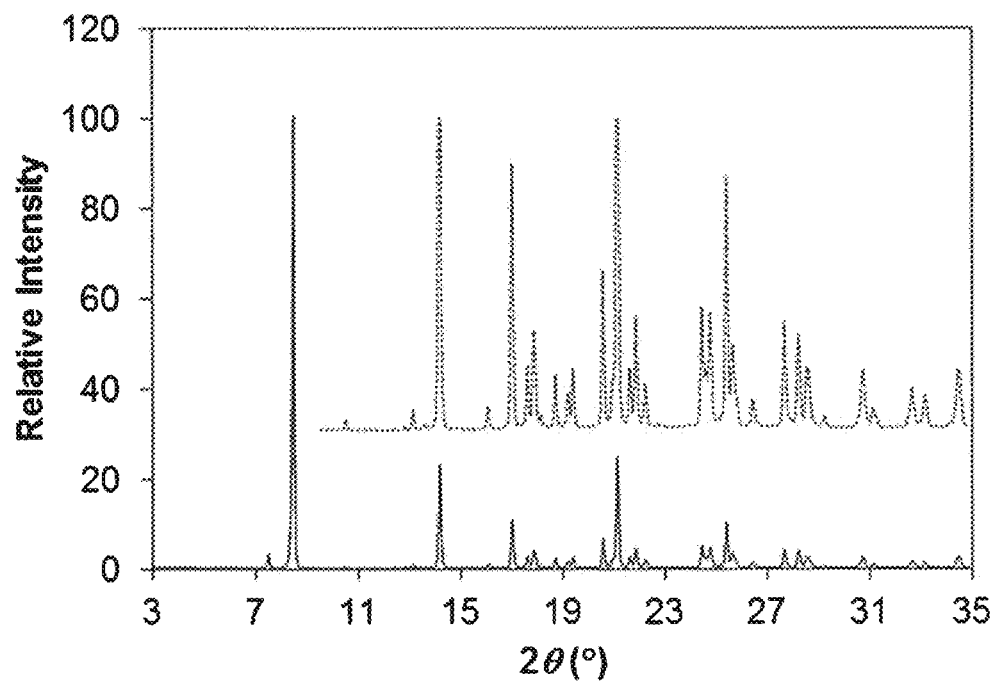
FIG. 1 shows a powder x-ray diffraction (PXRD) pattern of the crystalline non-solvated (2R,4R)-5-(5'-chloro-2'-fluorobiphenyl-4-yl)-2-hydroxy-4-[(5-methyl-oxazole-2-carbonyl)amino]pentanoic acid (1').

In one aspect, the invention relates to (2R,4R)-5-(5'-chloro-2'-fluorobiphenyl-4-yl)-2-hydroxy-4-[(5-methyl-oxazole-2-carbonyl)amino]pentanoic acid (1), or a pharmaceutically acceptable salt thereof.

Compound 1 of the invention contains two chiral centers and therefore, a compound of such a structure may exist in various stereoisomeric forms. Specifically, the carbon atoms may have a particular (R,R), (S,S), (S,R), or (R,S) configuration or are enriched in a stereoisomeric form having such configuration. Compound 1, as shown and named is in the (R, R) configuration. It will be understood by those skilled in the art that minor amounts of the other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Compound 1 of the invention possesses neprilysin (NEP) inhibition activity, that is, the compound is able to inhibit enzyme-catalytic activity. One measure of the ability of a compound to inhibit NEP activity is the inhibition constant ($pK_i$). The $pK_i$ value is the negative logarithm to base 10 of the dissociation constant ($K_i$), which is typically reported in molar units. The compound of the invention has a $pK_i$ at NEP≥9.0. Other properties and utilities of Compound 1 can be demonstrated using in vitro and in vivo assays that are well-known to those skilled in the art, including, inter alia, those described in U.S. Pat. No. 8,586,536.

Compound 1, as well as those compounds used in its synthesis, may also include isotopically-labeled compounds, that is, where one or more atoms have been enriched with atoms having an atomic mass different from the atomic mass predominately found in nature. Examples of isotopes that may be incorporated into the compounds described in this invention, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest is Compound 1 enriched in tritium or carbon-14 which can be used, for example, in tissue distribution studies; Compound 1 enriched in deuterium especially at a site of metabolism resulting, for example, in a compound having greater metabolic stability; and Compound 1 enriched in a positron emitting isotope, such as $^{11}C$, $^{18}F$, $^{15}O$, an $^{13}N$, which can be used, for example, in Positron Emission Topography (PET) studies.

Chemical structures are named herein according to IUPAC conventions as implemented in ChemDraw software (Perkin Elmer, Inc., Cambridge, Mass.).

Definitions

When describing the compound, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "about" or "approximately" when used in the context of thermal behavior of Compound 1 is defined as ±1-3° C. The term "approximate" when used in the context of % dose of Compound 1 excreted in the urine is defined by a margin of error that is typically about twice the standard deviation or the half-width of a 95 percent confidence interval. The term "approximate" in other areas of the disclosure may be used to indicate standard deviation or the amount of variation or dispersion of a set of data values.

The term "controlled-release" as used herein is synonymous with sustained-release and extended-release and relates to amount of drug delivered over extended period of time in a subject. Generally, controlled-release tablets and capsules release the active into the subject over time periods of about 8-, 12-, 16-, and 24-hours. On the other hand, the term "immediate-release" refers to the active being released in a subject within a small period of time, typically less than about 30 minutes. The term "delayed-release" is directed to tablets and capsules that release the pharmaceutical dose after a set period of time. These dosage forms are usually enteric-coated in order to prevent release in the stomach but allow the release in the intestinal track.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

In general, in describing pharmaceutical solids, the term "non-solvated" implies "without solvent". Thus, when the crystalline form of the invention is described as being "non-solvated," it is meant that the crystalline particles essentially contain only (2R,4R)-5-(5'-chloro-2'-fluorobiphenyl-4-yl)-2-hydroxy-4-[(5-methyloxazole-2-carbonyl)amino]pentanoic acid molecules; the form contains no significant amounts of other lattice-included solvent molecules or in other words, solvent is not significantly incorporated into the crystal lattice. The term "non-solvated" also means non-hydrated or anhydrous when water is a solvent.

The term "melting point" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "subject" or "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

General Synthetic Procedures

Compound 1 of the invention and its crystalline non-solvated form can be synthesized from readily available starting materials as described below and in the Examples. It will be appreciated that where typical or preferred process conditions (i.e., reaction temperatures, times, mole ratios of reactants, solvents, pressures, etc.) are given, other process conditions can also be used unless otherwise stated. It will be appreciated that while specific process conditions (i.e., crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature means a temperature within the range commonly associated with the ambient temperature in a laboratory environment, and will typically be in the range of about 15° C. to about 30° C., such as about 20° C. to about 25° C. In other instances, reactions or crystallizations were conducted at room temperature and the temperature was actually measured and recorded.

Any molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

In one embodiment, the invention relates to (2R,4R)-5-(5'-chloro-2'-fluorobiphenyl-4-yl)-2-hydroxy-4-[(5-methyloxazole-2-carbonyl)amino]pentanoic acid (1) or a pharmaceutically acceptable salt thereof.

In another embodiment, Compound 1 can be prepared by coupling (2R, 4R)-4-amino-5-(5'-chloro-2'-fluorobiphenyl-4-yl)-2-hydroxypentanoic acid ethyl ester with 2-methyloxazole-2-carboylic acid to yield Compound 1.

In yet another embodiment, Compound 1 can be prepared by (a) combining 2-methyloxazole-2-carboylic acid and N,N,N',N'-tetramethyl-O-(7-azabenzotriazol-1-yl)uronium hexafluorophosphate (HATU) in N,N-dimethylformamide (DMF) and stirring at room temperature; (b) adding (2R, 4R)-4-amino-5-(5'-chloro-2'-fluorobiphenyl-4-yl)-2-hydroxypentanoic acid ethyl ester and N,N-diisopropylethylamine and stirring at room temperature; (c) isolating and then dissolving the resulting solids in dry ethanol and dry tetrahydrofuran; (d) adding a solution of lithium hydroxide in water; and (e) isolating the resulting solids to yield Compound 1. The resulting solids in previous steps (c) and (e) may also be purified by chromatography.

Preparation of the crystalline form is generally conducted in a suitable inert diluent, examples of which include, but are not limited to, acetone, acetonitrile, ethyl acetate, methyl ethyl ketone, methanol, ethanol, isopropanol, isobutanol, dichloromethane, methyl t-butyl ether, cyclopentyl methyl ether, hexanes, and the like, and mixtures thereof, optionally containing water. Mixtures of inert diluents (also referred to as solvent systems) include acetone with water, acetonitrile with water, ethanol and ethyl acetate, ethyl acetate and hexanes, and lower alcohols ($C_{1-6}$alkyl-OH) with water, for example, methanol and water and isopropanol and water. Particularly suitable solvent systems include ethyl acetate and hexanes. Upon completion of the crystallization, the crystalline compound can be isolated from the reaction mixture by any conventional means such as precipitation, filtration, concentration, centrifugation, dried in vacuo, and the like.

In one embodiment, the invention relates to a crystalline form of (2R, 4R)-5-(5'-chloro-2'-fluorobiphenyl-4-yl)-2-hydroxy-4-[(5-methyloxazole-2-carbonyl)amino]pentanoic acid. In another embodiment, the crystalline form is a non-solvated crystal form of (2R,4R)-5-(5'-chloro-2'-fluorobiphenyl-4-yl)-2-hydroxy-4-[(5-methyloxazole-2-carbonyl)amino]pentanoic acid (1').

In another embodiment, the crystalline form (1') can be prepared by (a) dissolving (2R, 4R)-5-(5'-chloro-2'-fluorobiphenyl-4-yl)-2-hydroxy-4-[(5-methyloxazole-2-carbonyl)amino]pentanoic acid (1) in ethyl acetate and hexanes to complete dissolution; and (b) isolating the resulting solids to yield the crystalline form (1'). Step (a) is generally conducted at room temperature.

In yet another embodiment, the crystalline form (1') can be prepared by (a) coupling (2R,4R)-4-amino-5-(5'-chloro-2'-fluorobiphenyl-4-yl)-2-hydroxypentanoic acid ethyl ester with sodium 5-methyloxazole-2-carboylate to yield (2R, 4R)-5-(5'-chloro-2'-fluorobiphenyl-4-yl)-2-hydroxy-4-[(5-methyloxazole-2-carbonyl)amino]pentanoic acid; (b) treating (2R,4R)-5-(5'-chloro-2'-fluorobiphenyl-4-yl)-2-hydroxy-4-[(5-methyloxazole-2-carbonyl)amino]pentanoic acid with ethyl acetate and hexanes to complete dissolution; and (c) isolating the resulting solids to yield crystalline form (1').

Crystalline Properties

As is well known in the field of powder x-ray diffraction (PXRD) analysis, relative peak heights of PXRD patterns are dependent on a number of factors relating to sample preparation and instrument geometry, while peak positions are relatively insensitive to experimental details. PXRD, differential scanning calorimetry (DSC), thermal gravimetric analyses (TGA), and dynamic moisture sorption (DMS) assessment (also known as moisture sorption-desorption analysis) were performed as described herein.

In another aspect, the invention relates to (2R,4R)-5-(5'-chloro-2'-fluorobiphenyl-4-yl)-2-hydroxy-4-[(5-methyl-oxazole-2-carbonyl)amino] pentanoic acid in crystalline form. In another embodiment, the crystalline form is non-solvated (1') and characterized by a PXRD pattern in which the peak positions are substantially in accordance with those shown in FIG. 1. The inset with dotted lines in FIG. 1 shows the y-zoomed pattern, to accentuate peaks with lower intensity.

Peaks with relative intensities greater than 1% in area are listed in the table below. This pattern shows sharp diffraction peaks in the range of 5-35° in 2θ. These and other peaks in the diffraction pattern can be used to identify this form.

| 2θ* | d (Å) | Area | Area % |
|---|---|---|---|
| 7.51 | 11.77 | 769.8 | 3.0 |
| 8.48 | 10.42 | 25471.2 | 100.0 |
| 14.19 | 6.24 | 6344.6 | 24.9 |
| 16.09 | 5.51 | 246.5 | 1.0 |
| 17.03 | 5.20 | 3143.3 | 12.3 |

-continued

| 2θ*   | d (Å) | Area   | Area % |
|-------|-------|--------|--------|
| 17.62 | 5.03  | 771.3  | 3.0    |
| 17.87 | 4.96  | 1491.9 | 5.9    |
| 18.70 | 4.74  | 579.1  | 2.3    |
| 19.21 | 4.62  | 538.0  | 2.1    |
| 19.40 | 4.57  | 653.4  | 2.6    |
| 20.59 | 4.31  | 1862.4 | 7.3    |
| 21.15 | 4.20  | 7421.4 | 29.1   |
| 21.64 | 4.10  | 600.3  | 2.4    |
| 21.88 | 4.06  | 1289.8 | 5.1    |
| 22.25 | 3.99  | 424.4  | 1.7    |
| 24.45 | 3.64  | 1608.3 | 6.3    |
| 24.78 | 3.59  | 1954.8 | 7.7    |
| 25.41 | 3.50  | 3196.3 | 12.5   |
| 25.67 | 3.47  | 1909.9 | 7.5    |
| 26.43 | 3.37  | 419.7  | 1.6    |
| 27.67 | 3.22  | 1377.9 | 5.4    |
| 28.22 | 3.16  | 1430.4 | 5.6    |
| 28.55 | 3.12  | 1242.2 | 4.9    |
| 30.73 | 2.91  | 1221.6 | 4.8    |
| 31.10 | 2.87  | 439.5  | 1.7    |
| 32.64 | 2.74  | 861.6  | 3.4    |
| 33.14 | 2.70  | 645.9  | 2.5    |
| 34.46 | 2.60  | 1246.1 | 4.9    |

*2θ values are reported as value ±0.20.

Thus, in one embodiment, crystalline form 1' is characterized by PXRD pattern comprising diffraction peaks at 2θ values of 8.48±0.20, 14.19±0.20, 17.03±0.20, 21.15±0.20, and 25.41±0.20.

In another embodiment, the crystalline form 1' is characterized by PXRD pattern comprising diffraction peaks at 2θ values of 7.51±0.20, 8.48±0.20, 14.19±0.20, 17.03±0.20, 17.62±0.20, 17.87±0.20, 20.59±0.20, 21.15±0.20, 21.88±0.20, 24.45±0.20, 24.78±0.20, 25.41±0.20, 25.67±0.20, 27.67±0.20, and 28.22±0.20.

In another embodiment, the crystalline form 1' is further characterized by having one or more additional diffraction peaks at 2θ values selected from 16.09±0.20, 18.70±0.20, 19.21±0.20, 19.40±0.20, 21.64±0.20, 22.25±0.20, 26.43±0.20, 28.55±0.20, 30.73±0.20, 31.10±0.20, 32.64±0.20, 33.14±0.20, and 34.46±0.20; and in yet another embodiment the crystalline compound is further characterized by having three or more such additional diffraction peaks.

Figure 2:
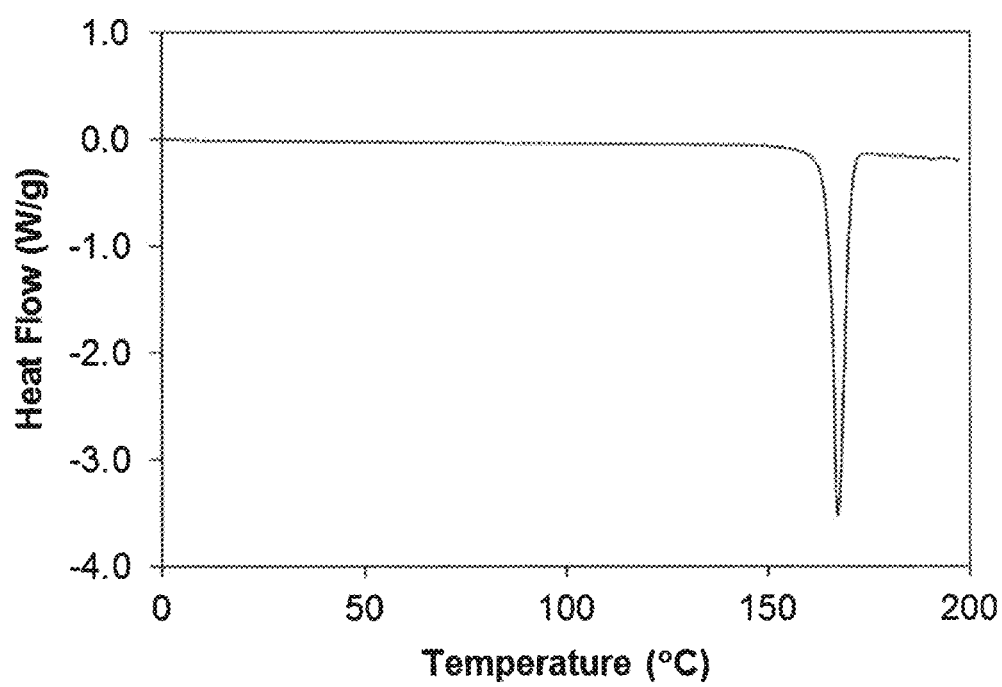
FIG. 2 shows a differential scanning calorimetry (DSC) thermogram of the crystalline non-solvated form (1').

In one embodiment, crystalline form 1' is characterized by the DSC thermogram or differential scanning calorimetry trace substantially in accordance with that shown in FIG. 2. The crystalline form 1' is characterized by a differential scanning calorimetry trace recorded at a heating rate of 10° C. per minute which shows a maximum in endothermic heat flow at a temperature between about 165° C. and about 169° C. The DSC thermogram or differential scanning calorimety trace illustrates a melting endotherm with a peak at about 167.1° C., onset at 165.2° C., and with an area under the endotherm corresponding to 114 J/g. Decomposition of the compound coincides with melting and the contribution of 114 J/g towards melting enthalpy is not established.

Figure 3:
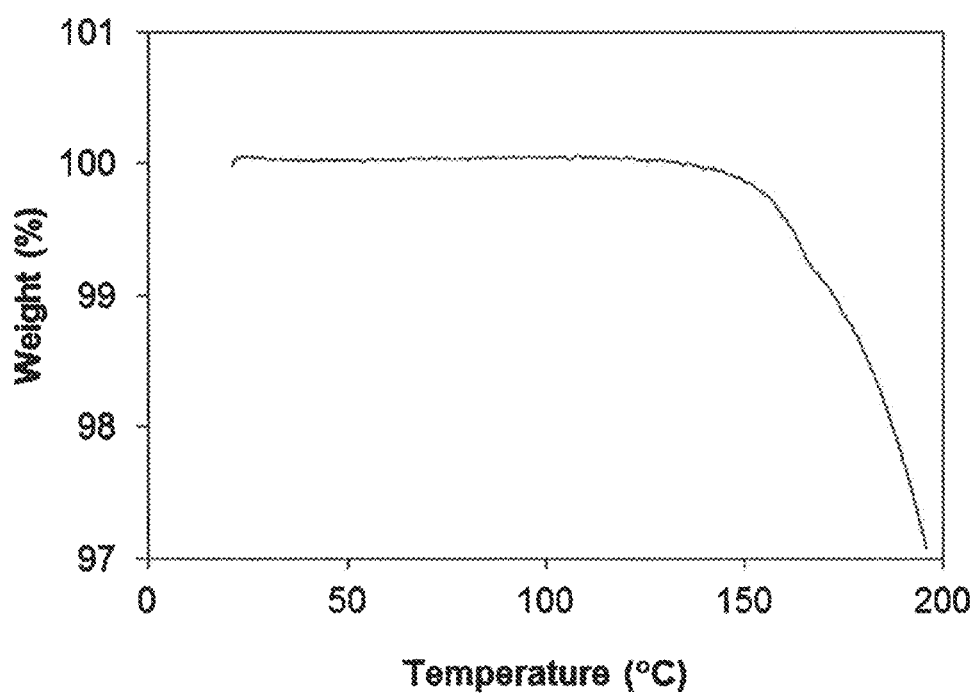
FIG. 3 shows a thermal gravimetry profile for the crystalline non-solvated form (1').

In one embodiment, crystalline form 1' is characterized by the TGA profile in FIG. 3. This profile shows no mass loss until about 150° C.; the crystalline compound decomposes after melting, as seen by significant weight loss occurring at an onset of approximately 159° C.

Figure 4:
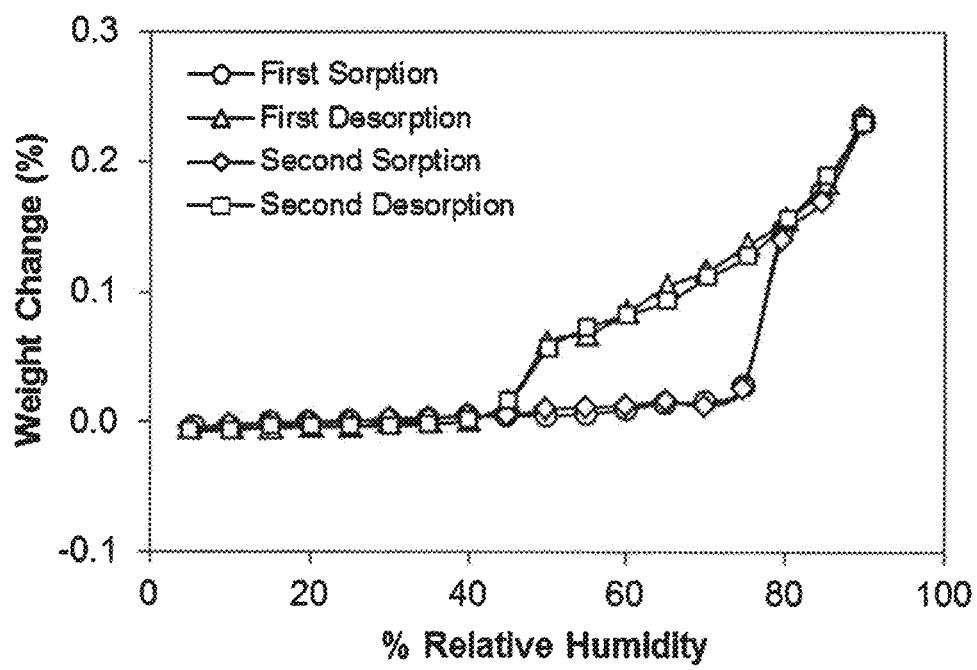
FIG. 4 shows a dynamic moisture sorption (DMS) isotherm of the crystalline non-solvated form (1').

In one embodiment, crystalline form 1' is characterized by the DMS isotherm in FIG. 4. This form is a non-hygroscopic solid. The total moisture gain observed is less than 0.025% by weight when exposed to 5-70% relative humidity. The total moisture gain is less than 0.235% by weight when exposed to 5-90% relative humidity. No significant hysteresis is found between two consecutive sorption-desorption cycles. The solid obtained after sorption-desorption cycles showed the same PXRD pattern as the starting material, indicating no change in form after this experiment.

Figure 5:
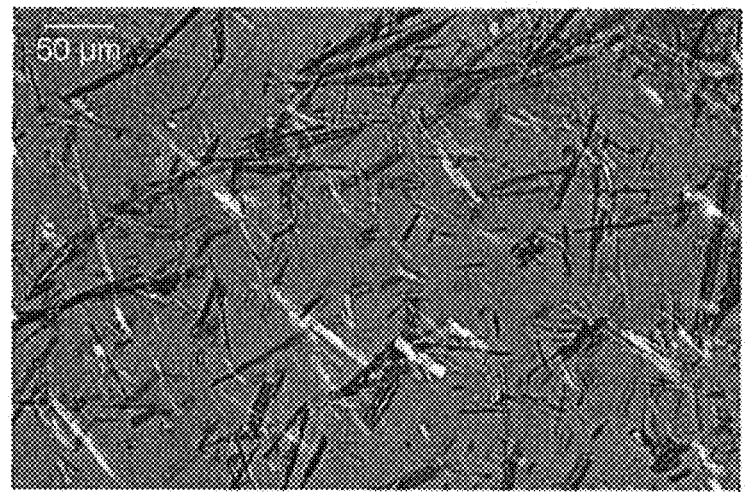
FIG. 5 is a polarized light microscope (PLM) image of the crystalline non-solvated form (1').

The crystalline form 1' can be characterized by the PLM image in FIG. 5, which shows this form as being crystalline, birefringent, with thin needle to thin lath shaped particles.

Utility

The in vitro-to-in vivo extrapolation of drug behavior in a subject continues to improve (see, e.g., Chiba et al., AAPS J., 2009 June; 11(2): 262-276). In the present invention, in vitro human neprilysin inhibitor activity was assessed (Assay 1) in order to determine neprilysin inhibitory activity of Compound 1. A threshold of $pK_i \geq 9.0$ was met. However, additional in vivo experiments were further performed in order to more accurately predict the behavior of Compound 1 in a subject.

Regarding in vivo behavior, there are several properties that useful in evaluating whether a sufficient amount of the drug will be delivered to the plasma in order to achieve the necessary therapeutic benefit, for example low plasma clearance across all species tested, high oral bioavailability, favorable potentiation of the cyclic guanosine monophosphate (cGMP) response and low renal clearance for those subjects with compromised kidney function.

For the present invention, oral and intravenous pharmacokinetic studies were conducted in both rat and dog species in order to determine the oral bioavailability of the Compound 1 as compared to other neprilysin inhibitors (Assay 2). This assay was also used to determine the rate of plasma clearance for these compounds; a low clearance rate is believed to be predictive of how long the compound is expected to remain in circulation, i.e., its in vivo stability and persistence without identifying the individual elimination processes involved. Additionally, oral bioavailability and rate of plasma clearance in monkey specie was conducted (Assay 4).

Pharmacokinetic/pharmacodynamic studies were conducted in rats in order to determine the level of neprilysin inhibition that is obtained with Compound 1 as compared to other neprilysin inhibitors (Assay 3). In this assay the level of cyclic guanosine monophosphate (cGMP) is measured. cGMP is a downstream effector molecule of natriuretic peptide receptor binding and thus serves as an effective in vivo biomarker of natriuretic peptide activity. The level of cGMP increases when an animal is administered a neprilysin inhibitor as compared to placebo. One embodiment of the invention relates to a method of increasing atrial natriuretic peptide (ANP) or cGMP basal levels in a subject with hypertension, heart failure, or renal disease comprising administering to a subject a therapeutically effective amount of the Compound 1 or crystalline form thereof Levels of ANP and cGMP are measured in either urine or plasma or both in a subject. In another embodiment, the level of ANP or cGMP is elevated at least ≥1.1-fold, ≥1.2-fold, ≥1.3-fold, ≥1.4-fold, ≥1.5-fold, ≥2-fold, ≥3-fold, ≥4-fold, or ≥5-fold over a 24-hour period in a subject when administered a therapeutically effective amount of Compound 1 or crystalline form thereof.

Compound 1 inhibits the NEP enzyme, and therefore is expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of Compound 1. For example, by inhibiting NEP, Compound 1 is expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, this compound is expected to have other physiological actions, for example, on the renal, central nervous, reproductive and gastrointestinal systems.

Drugs are removed from a subject body by various elimination processes which are categorized generally as excretion and biotransformation. Excretion relates to the removal of the intact non-volatile drug mainly by renal (kidney) to bladder to urine while other pathways of excretion include bile (liver), sweat, saliva, milk (via lactation) or other bodily fluids. Volatile drugs like alcohol and gaseous anesthetics are excreted via the lungs into expired air. On the other hand, biotransformation, or drug metabolism, relates to a drug being chemically converted in the body to a metabolite and is usually an enzymatic process. Exception to this is when a drug is chemically changed non-enzymatically, e.g., ester hydrolysis. Enzymes involved in biotransformation of drugs are located mainly in the liver. Other tissues such as kidney, lung, small intestine and skin also contain metabolic enzymes.

Pharmacokinetic studies can also be used to investigate elimination pathways in a subject, e.g., renal clearance via excretion of the administered drug in urine over time. The renal excretion of Compound 1 in rat, dog and monkey species was conducted to assess kidney excretion as an elimination pathway (Assay 5). This elimination pathway is important for subjects that have compromised kidney function and need therapies that are minimally cleared by kidney excretion. In one embodiment, the renal excretion of Compound 1 or crystalline form thereof in the subject is approximately ≤15%, ≤10%, ≤5%, ≤3%, ≤2%, ≤1% or ≤0.5% of the administered dose over 24 hours.

As described in the assay section below, included along with Compound 1 in an in vitro NEP enzyme assay, and in in vivo determinations of plasma clearance, oral bioavailability, and renal excretion in multiple animal species, were comparator compounds of similar chemical structure. Surprisingly, significant differences in results were observed. While individual comparator compounds exhibited properties, similar to those of Compound 1 in one or more assays, only Compound 1 exhibited, at the same time, high inhibitory activity of human neprilysin, high oral bioavailability, low plasma clearance, increased potentiation of cGMP and low renal excretion expected to lead to particular utility in the treatment of disease.

Cardiovascular Diseases

By potentiating the effects of vasoactive peptides like the natriuretic peptides and bradykinin, Compound 1 is expected to find utility in treating and/or preventing medical conditions such as cardiovascular diseases. See, for example, Rogues et al. (1993) *Pharmacol. Rev.* 45:87-146 and Dempsey et al. (2009) *Amer. J. of Pathology* 174(3): 782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure. Thus, one embodiment of the invention relates to a method for treating hypertension, particularly primary hypertension or pulmonary arterial hypertension, comprising administering to a patient a therapeutically effective amount of Compound 1.

For treatment of primary hypertension, the therapeutically effective amount is typically the amount that is sufficient to lower the patient's blood pressure. This would include both mild-to-moderate hypertension and severe hypertension. When used to treat hypertension, Compound 1 may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting β-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, the compound of the invention is combined with an $AT_1$ receptor antagonist, a calcium channel blocker, a diuretic, or a combination thereof, and used to treat primary hypertension. In another particular embodiment of the invention, the compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension Compound 1 may be administered in combination with other therapeutic agents such as α-adrenergic receptor antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, Compound 1 is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of Compound 1. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, Compound 1 may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting $\beta$-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, Compound 1 is combined with an aldosterone antagonist, a $\beta_1$-adrenergic receptor antagonist, an $AT_1$ receptor antagonist, or a diuretic, and used to treat congestive heart failure.

Diarrhea

As a NEP inhibitor, Compound 1 is expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marçais-Collado (1987) *Eur. J. Pharmacol.* 144(2):125-132. When used to treat diarrhea, compound 1 may be combined with one or more additional antidiarrheal agents.

Renal Diseases

By potentiating the effects of vasoactive peptides like the natriuretic peptides and bradykinin, Compound 1 is expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases in a renally-impaired subject. Renal diseases of particular interest include diabetic nephropathy, chronic kidney disease, proteinuria, and particularly acute kidney injury (caused, for example, by cardiovascular surgery, chemotherapy, or the use of contrast dyes in medical imaging) or acute renal failure (see Sharkovska et al. (2011) *Clin. Lab.* 57:507-515 and Newaz et al. (2010) *Renal Failure* 32:384-390).

A renally-impaired subject that has chronic kidney disease (CKD) may be classified according to the National Kidney Foundation Kidney Disease Outcomes Quality Initiative (NKF KDOQI) Guidelines. Once chronic kidney disease is established, i.e., kidney damage or glomerular filtration rate (GFR) <60 mL/min/1.73 $m^2$ for ≥3 months, the stage of disease may be assigned according to KDOQI CKD classification. These include Stage 1 (kidney damage with normal or increased GFR): GFR ≥90; Stage 2 (kidney damage with mild decreased GFR): GFR 60-89; Stage 3 (Moderate decreased GFR): GFR 30-59; Stage 4 (severe decrease GFR): GFR 15-29; and Stage 5 (kidney failure): GFR <15 (or dialysis). GFR is defined in units of mL/min/1.73 $m^2$.

One embodiment includes a method of treating a renally-impaired subject comprising administering a therapeutically effective amount of Compound 1 or a crystalline form thereof, specifically crystalline form 1'. This method further includes treating a renally-impaired subject with hypertension or heart failure. When used to treat renal disease, Compound 1 or a crystalline form thereof, specifically crystalline form 1' may be administered in combination with other therapeutic agents such as angiotensin-converting enzyme inhibitors, $AT_1$ receptor antagonists, and diuretics.

Another embodiment includes a method of treating a renally-impaired subject having chronic kidney disease with an estimated glomular filtration rate (eGFR) between 60 mL/min/1.73 $m^2$ and 15 mL/min/1.73 $m^2$ comprising administering to a patient a therapeutically effective amount of Compound 1 or a crystalline form thereof, specifically crystalline form 1'. Another embodiment includes a method of treating a renally-impaired subject having chronic kidney disease with an estimated glomular filtration rate (eGFR) ≥90 mL/min/1.73 $m^2$ (Stage 1) or an eGFR <15 mL/min/1.73 $m^2$ (Stage 5) comprising administering to a patient a therapeutically effective amount of Compound 1 or a crystalline form thereof, specifically crystalline form 1'. For purposes of this invention, severe kidney disease may be classified as an eGFR <30 mL/min/1.73 $m^2$. In yet another embodiment, a method of treating a renally-impaired subject having chronic kidney disease classified as Stage 1, Stage 2, Stage 3, Stage 4, Stage 5 or eGFR ranges covering one or more of these stages with Compound 1 or a crystalline form thereof, specifically crystalline form 1' is included.

Preventative Therapy

By potentiating the effects of the natriuretic peptides, Compound 1 is also expected to be useful in preventative therapy, due to the antihypertrophic and antifibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, Compound 1 is expected to be useful to treat glaucoma. See, for example, Diestelhorst et al. (1989) *International Ophthalmology* 12:99-101. When used to treat glaucoma, Compound 1 may be combined with one or more additional antiglaucoma agents.

Pain Relief

As a NEP inhibitor, Compound 1 is expected to inhibit the degradation of endogenous enkephalins and thus such compound may also find utility as an analgesic. See, for example, Rogues et al. (1980) *Nature* 288:286-288 and Thanawala et al. (2008) *Current Drug Targets* 9:887-894. When used to treat pain, Compound 1 may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-HT$_{1D}$ serotonin receptor agonists, and tricyclic antidepressants.

Other Utilities

Due to its NEP inhibition properties, Compound 1 is also expected to be useful as an antitussive agent, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, compound 1 is expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, the compound of the invention may be combined with one or more of the following secondary agents: PDE-V inhibitors, dopamine agonists, estrogen receptor agonists and/or antagonists, androgens, and estrogens. Due to its NEP inhibition property, Compound 1 is also expected to have anti-inflammatory properties, and is expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to its NEP inhibition property, Compound 1 is also expected to be useful in providing protection from nerve impairment caused by diabetes or diet induced obesity.

The amount of Compound 1 administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of Compound 1 will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Compound 1 also finds utility as an intermediate useful for the preparation of crystalline forms of Compound 1, including, for example, crystalline form 1'.

Research Tools

Since Compound 1 possesses NEP enzyme inhibition activity, it is also useful as a research tool for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of Compound 1.

When used as a research tool, a biological system or sample comprising a NEP enzyme is typically contacted with a NEP enzyme-inhibiting amount of Compound 1. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, Compound 1 can be used as a research tool for evaluating other chemical compounds, and thus is also useful in screening assays to discover, for example, new compounds having NEP-inhibiting activity. In this manner, Compound 1 is used as a standard in an assay to allow comparison of the results obtained with a test compound and with Compound 1 to identify those test compounds that have about equal or superior activity, if any. For example, pK$_i$ data for a test compound or a group of test compounds is compared to the pK$_i$ data for Compound 1 to identify those test compounds that have the desired properties, for example, test compounds having a $pK_i$ value equal or superior to the compound of the invention. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with Compound 1 to provide a second assay value; wherein step (a) is conducted either before, after or concurrently with step (b); and (c) comparing the first assay value from step (a) with the second assay value from step (b). Exemplary biological assays include a NEP enzyme inhibition assay.

Still another aspect of the invention relates to a method of studying a biological system or sample comprising a NEP enzyme, the method comprising: (a) contacting the biological system or sample with Compound 1; and (b) determining the effects caused by the compound on the biological system or sample.

Pharmaceutical Compositions and Formulations

Compound 1 is typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, Compound 1 may be administered, for example orally, in multiple doses per day (for example, two, three, or four times daily), in a single daily dose or a single weekly dose. It will be understood that any form of Compound 1, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and Compound 1. The composition may contain other therapeutic and/or formulating agents if desired. When discussing compositions, "Compound 1" may also be referred to herein as the "active agent," to distinguish it from other components of the formulation, such as the carrier. Thus, it is understood that the term "active agent" includes Compound 1 as well as its pharmaceutically acceptable salts.

The pharmaceutical compositions of the invention typically contain a therapeutically effective amount of Compound 1. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20*th* Edition, Lippincott Williams & White, Baltimore, Md. (2000); and H. C. Ansel et al., *Pharmaceutical Dosage Forms and Drug Delivery Systems*, 7*th* Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; fatty acid salts, such as magnesium stearate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

In one embodiment of the invention, the pharmaceutically acceptable carrier is magnesium stearate. For example, the pharmaceutical composition may comprise Compound 1 or a crystalline form 1' and magnesium stearate in a ratio of about 3:1 to about 10:1 of Compound 1 or a crystalline form 1' to magnesium stearate. Other ratios of Compound 1 or a crystalline form 1' to magnesium stearate include, but are not limited to, 1:1, 5:1, 15:1, 20:1, 25:1, 30:1 and 50:1.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate, dicalcium phosphate, or magnesium stearate. Solid dosage forms may also comprise fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents. For the purpose of this invention, the terms "pharmaceutically acceptable carriers" are inclusive of all the terms such as carriers, fillers or extenders, binders, humectants, solution retarding agents, wetting agents, absorbents, lubricants, coloring agents and buffering agents described above.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

One embodiment of the invention includes an oral dosage form comprising Compound 1 or crystalline form 1' in a capsule, tablet, liquid or suspension. Another embodiment of the invention relates to an oral dosage form where a release of the Compound 1 or crystalline form 1' in a subject is an immediate, controlled or delayed release. If a capsule is used as an oral dosage form, another embodiment includes the capsule being comprised of gelatin, polysaccharides or synthetic polymers. In a particular embodiment, the capsule comprises hydroxypropyl methylcelluose.

Suitable capsule materials according to the invention are selected from gelatin, cellulose derivatives, starch, starch derivatives, chitosan and synthetic plastics. If gelatin is used as the capsule material, it may be used in admixture with other additives selected from polyethyleneglycol (PEG), glycerol, sorbitol, polypropyleneglycol, PEO-PPO block copolymers and other polyalcohols and polyethers. When a cellulose derivative is used as the capsule material, hydroxypropylmethylcellulose, hydroxypropylcellulose, methylcellulose, hydroxymethylcellulose and hydroxyethylcellulose are preferred polymers. If synthetic plastics are used as a capsule material, polyethylene, polycarbonate, polyester, polypropylene and polyethylene terephthalate are preferred materials. Particularly preferred are polyethylene, polycarbonate or polyethylene terephthalate.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compound 1 and compositions thereof can also be administered parenterally, for example, by subcutaneous, intravenous, intramuscular, or intraperitoneal injection. For such administration, the active agent is provided in a sterile solution, suspension, or emulsion. Exemplary solvents for preparing such formulations include water, saline, electrolytes, low molecular weight alcohols such as propylene glycol and polyethylene glycol, oils, amino acids, gelatin, sugars, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages that may be present in the compound. These formulations may be rendered sterile by use of a sterile injectable medium, a sterilizing agent, filtration, irradiation, or heat.

Representative physiologically-acceptable aqueous carriers include, by way of example, Sterile Water for Injection, USP; Dextrose Injection, USP (e.g., 2.5, 5.0, 10, 20% dextrose, including 5% Dextrose Injection (D5/W)); Dextrose and Sodium Chloride Injection, USP (e.g., dextrose varying from 2.5 to 10% and sodium chloride varying from 0.12 (19 mEq sodium) to 0.9% (154 mEq sodium)); Mannitol Injection, USP, (e.g., 5, 10, 15, 20 and 25% mannitol); Ringer's Injection, USP (e.g., 147 mEq sodium, 4 mEq potassium, 4.5 mEq calcium and 156 mEq chloride per liter); Lactated Ringer's Injection, USP (e.g., 2.7 mEq calcium, 4 mEq potassium, 130 mEq sodium, and 28 mEq lactate per liter); Sodium Chloride Injection, USP (e.g., 0.9% sodium chloride) and the like.

When administered to a patient, the Compound 1 will typically be diluted in about 0.5 mL to about 10 mL of the aqueous carrier per mg of the Compound 1, such as about 0.6 to about 8 mL per mg.

In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions. In one embodiment of the invention, an intravenous dosage form comprises Compound 1 or crystalline form 1' in a buffered solution.

In one embodiment, Compound 1 or a pharmaceutical composition thereof is a lyophilized powder. Typically, the lyophilized powder is sterile and is packaged in a hermetically-sealed vial or ampoule or similar container.

Compound 1 can also be administered transdermally using known transdermal delivery systems and excipients. For example, Compound 1 can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

Compound 1 may be useful as the sole treatment of a disease or may be combined with one or more additional therapeutic agents in order to obtain the desired therapeutic effect. Thus, in one embodiment, pharmaceutical compositions of the invention contain other drugs that are co-administered with Compound 1. For example, the composition may further comprise one or more drugs (also referred to as "secondary agents(s)"). Such therapeutic agents are well known in the art, and include adenosine receptor antagonists, α-adrenergic receptor antagonists, $β_1$-adrenergic receptor antagonists, $β_2$-adrenergic receptor agonists, dual-acting β-adrenergic receptor antagonist/$α_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

A specific embodiment includes a pharmaceutical composition comprising Compound 1 or crystalline form thereof and an $AT_1$ receptor antagonist, an angiotensin-converting enzyme inhibitor, a phosphodiesterase (PDE) inhibitor, a renin inhibitor, a diuretic, or combinations thereof, and optionally one or more pharmaceutically acceptable carriers.

Accordingly, in yet another aspect of the invention, a pharmaceutical composition comprises Compound 1, a second active agent, and a pharmaceutically acceptable carrier. Third, fourth etc. active agents may also be included in the composition. In combination therapy, the amount of compound 1 that is administered, as well as the amount of secondary agents, may be less than the amount typically administered in monotherapy.

Compound 1 may be physically mixed with the second active agent to form a composition containing both agents; or each agent may be present in separate and distinct compositions which are administered to the patient simultaneously or at separate times. For example, Compound 1 can be combined with a second active agent using conventional procedures and equipment to form a combination of active agents comprising Compound 1 and a second active agent. Additionally, the active agents may be combined with a pharmaceutically acceptable carrier to form a pharmaceutical composition comprising Compound 1, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of Compound 1, ranging anywhere from concurrent with administration of the compound of the invention to about 24 hours post-dose. This is also referred to as sequential administration. Thus, Compound 1 can be orally administered simultaneously or sequentially with another active agent using two tablets, with one tablet for each active agent, where sequential may mean being administered immediately after administration of Compound 1 or at some predetermined time later (for example, one hour later or three hours later). It is also contemplated that the secondary agent may be administered more than 24 hours after administration of Compound 1. Alternatively, the combination may be administered by different routes of administration, that is, one orally and the other by inhalation.

In one embodiment, the kit comprises a first dosage form comprising Compound 1 and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with Compound 1 of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, Compound 1 is administered in combination with an adenosine receptor antagonist, examples of which include naxifylline, rolofylline, SLV-320, theophylline, and tonapofylline.

In one embodiment, Compound 1 is administered in combination with an α-adrenergic receptor antagonist, examples of which include doxazosin, prazosin, tamsulosin, and terazosin.

Compound 1 may also be administered in combination with a $\beta_1$-adrenergic receptor antagonist ("$\beta_1$-blocker"), examples of which include acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the $\beta_1$-blocker will be administered in an amount sufficient to provide from about 2-900 mg per dose.

In one embodiment, Compound 1 is administered in combination with a $\beta_2$-adrenergic receptor agonist, examples of which include albuterol, bitolterol, fenoterol, formoterol, indacaterol, isoetharine, levalbuterol, metaproterenol, pirbuterol, salbutamol, salmefamol, salmeterol, terbutaline, vilanterol, and the like. Typically, the $\beta_2$-adrenergic receptor agonist will be administered in an amount sufficient to provide from about 0.05-500 μg per dose.

In one embodiment, Compound 1 is administered in combination with an advanced glycation end product (AGE) breaker, examples of which include alagebrium (or ALT-711) and TRC4149.

In another embodiment, Compound 1 is administered in combination with an aldosterone antagonist, examples of which include eplerenone, spironolactone, and combinations thereof. Typically, the aldosterone antagonist will be administered in an amount sufficient to provide from about 5-300 mg per day.

In one embodiment, Compound 1 is administered in combination with an aminopeptidase N or dipeptidyl peptidase III inhibitor, examples of which include bestatin and PC18 (2-amino-4-methylsulfonyl butane thiol, methionine thiol).

Compound 1 can also be administered in combination with an angiotensin-converting enzyme (ACE) inhibitor, examples of which include accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day.

In another embodiment, Compound 1 is administered in combination with a dual-acting angiotensin-converting enzyme/neprilysin (ACE/NEP) inhibitor, examples of which include: AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*), 12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)-N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, Compound 1 is administered in combination with an angiotensin-converting enzyme 2 (ACE2) activator or stimulator.

In one embodiment, Compound 1 is administered in combination with an angiotensin-II vaccine, examples of which include ATR12181 and CYT006-AngQb.

In one embodiment, Compound 1 is administered in combination with an anticoagulant, examples of which include: coumarins such as warfarin; heparin; and direct thrombin inhibitors such as argatroban, bivalirudin, dabigatran, and lepirudin.

In yet another embodiment, Compound 1 is administered in combination with an anti-diabetic agent, examples of which include injectable drugs as well as orally effective drugs, and combinations thereof. Examples of injectable drugs include insulin and insulin derivatives. Examples of orally effective drugs include: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, Compound 1 is administered in combination with antidiarrheal treatments. Representative treatment options include oral rehydration solutions (ORS), loperamide, diphenoxylate, and bismuth subsalicylate.

In yet another embodiment, Compound 1 is administered in combination with an anti-glaucoma agent, examples of which include: α-adrenergic agonists such as brimonidine; β₁-adrenergic receptor antagonists; topical β₁-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, Compound 1 is administered in combination with an anti-lipid agent, examples of which include: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, Compound 1 is administered in combination with an anti-thrombotic agent, examples of which include: aspirin; anti-platelet agents such as clopidogrel, prasugrel, and ticlopidine; heparin, and combinations thereof.

In one embodiment, Compound 1 is administered in combination with an AT₁ receptor antagonist, also known as angiotensin II type 1 receptor blockers (ARBs). Representative ARBs include abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof.

Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compound 1 may also be administered in combination with a dual-acting agent, such as an AT₁ receptor antagonist/neprilysin inhibitor (ARB/NEP) inhibitor, examples of which include compounds described in U.S. Pat. Nos. 7,879,896 and 8,013,005, both to Allegretti et al., such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compound 1 may also be administered in combination with multifunctional angiotensin receptor blockers as described in Kurtz & Klein (2009) *Hypertension Research* 32:826-834.

In one embodiment, Compound 1 is administered in combination with a bradykinin receptor antagonist, for example, icatibant (HOE-140). It is expected that this combination therapy may present the advantage of preventing angioedema or other unwanted consequences of elevated bradykinin levels.

In one embodiment, Compound 1 is administered in combination with a calcium channel blocker, examples of which include amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, Compound 1 is administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl] acetamide (NK3201).

In one embodiment, Compound 1 is administered in combination with a diuretic, examples of which include: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and Na⁺ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compound 1 may also be administered in combination with an endothelin converting enzyme (ECE) inhibitor, examples of which include phosphoramidon, CGS 26303, and combinations thereof.

In a particular embodiment, Compound 1 is administered in combination with an endothelin receptor antagonist, examples of which include: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, and tezosentan.

In yet another embodiment, Compound 1 is administered in combination with one or more HMG-CoA reductase inhibitors, which are also known as statins. Representative statins include atorvastatin, fluvastatin, lovastatin, pitavastatin, pravastatin, rosuvastatin and simvastatin.

In one embodiment, Compound 1 is administered in combination with a monoamine reuptake inhibitor, examples of which include norepinephrine reuptake inhibitors such as atomoxetine, buproprion and the buproprion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, Compound 1 is administered in combination with a muscle relaxant, examples of which include: carisoprodol, chlorzoxazone, cyclobenzaprine, diflunisal, metaxalone, methocarbamol, and combinations thereof.

In one embodiment, Compound 1 is administered in combination with a natriuretic peptide or analog, examples of which include: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, Compound 1 is administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert* 17:861-876).

In another embodiment, Compound 1 is administered in combination with a neprilysin (NEP) inhibitor, examples of which include: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)-N-[N-(1-carboxy-2-phenylethyl)-L-phenylalanyl]-β-alanine) and its prodrug SCH-34826 ((S)-N-[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis A G); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, Compound 1 is administered in combination with a nitric oxide donor, examples of which include: nicorandil; organic nitrates such as pentaerythritol tetranitrate; and sydnonimines such as linsidomine and molsidomine.

In yet another embodiment, Compound 1 is administered in combination with a non-steroidal anti-inflammatory agent (NSAID), examples of which include: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, Compound 1 is administered in combination with an N-methyl d-aspartate (NMDA) receptor antagonist, examples of which include amantadine, dextromethorphan, dextropropoxyphene, ketamine, ketobemidone, memantine, methadone, and so forth.

In still another embodiment, Compound 1 is administered in combination with an opioid receptor agonist (also referred to as opioid analgesics). Representative opioid receptor agonists include: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, Compound 1 is administered in combination with a phosphodiesterase (PDE) inhibitor, particularly a PDE-V inhibitor. Representative PDE-V inhibitors include avanafil, lodenafil, mirodenafil, sildenafil (Revatio®), tadalafil (Adcirca®), vardenafil (Levitra®), and udenafil.

In another embodiment, Compound 1 is administered in combination with a prostaglandin analog (also referred to as prostanoids or prostacyclin analogs). Representative prostaglandin analogs include beraprost sodium, bimatoprost, epoprostenol, iloprost, latanoprost, tafluprost, travoprost, and treprostinil, with bimatoprost, latanoprost, and tafluprost being of particular interest.

In yet another embodiment, Compound 1 is administered in combination with a prostaglandin receptor agonist, examples of which include bimatoprost, latanoprost, travoprost, and so forth.

Compound 1 may also be administered in combination with a renin inhibitor, examples of which include aliskiren, enalkiren, remikiren, and combinations thereof.

In another embodiment, Compound 1 is administered in combination with a selective serotonin reuptake inhibitor (SSRI), examples of which include: citalopram and the citalopram metabolite desmethyl-citalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, Compound 1 is administered in combination with a 5-HT$_{1D}$ serotonin receptor agonist, examples of which include, triptans such as almotriptan, avitriptan, eletriptan, frovatriptan, naratriptan, rizatriptan, sumatriptan, and zolmitriptan.

In one embodiment, Compound 1 is administered in combination with a sodium channel blocker, examples of which include carbamazepine, fosphenytoin, lamotrigine, lidocaine, mexiletine, oxcarbazepine, phenytoin, and combinations thereof.

In one embodiment, Compound 1 is administered in combination with a soluble guanylate cyclase stimulator or activator, examples of which include ataciguat, riociguat, and combinations thereof.

In one embodiment, Compound 1 is administered in combination with a tricyclic antidepressant (TCA), examples of which include amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, Compound 1 is administered in combination with a vasopressin receptor antagonist, examples of which include conivaptan and tolvaptan.

Combined secondary therapeutic agents may also be helpful in further combination therapy with the compound of the invention. For example, the compound of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with Compound 1. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

The compound of the invention (50 g), 440 g spray-dried lactose and 10 g magnesium stearate are thoroughly blended. The resulting composition is then loaded into hard gelatin capsules (500 mg of composition per capsule). Alternately, Compound 1 (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, Compound 1 (30 g), a secondary agent (20 g), 440 g spray-dried lactose and 10 g magnesium stearate are thoroughly blended, and processed as described above.

Exemplary Gelatin Capsule Formulation for Oral Administration

Compound 1 (100 mg) is thoroughly blended with polyoxyethylene sorbitan monooleate (50 mg) and starch powder (250 mg). The mixture is then loaded into a gelatin capsule (400 mg of composition per capsule). Alternately, Compound 1 (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, Compound 1 (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Hydroxypropyl Methylcellulose (HPMC) Capsule for Oral Administration Compound 1 (50 mg or 100 mg) is loaded directly into a HPMC capsule.

Exemplary Tablet Formulation for Oral Administration

Compound 1 (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, Compound 1 (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, Compound 1 (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, Compound 1 (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of Compound 1 per 10 mL of suspension:

| Ingredients | Amount |
| --- | --- |
| Compound 1 | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |

-continued

| Ingredients | Amount |
| --- | --- |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, Compound 1(which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Parenteral IV Formulation for Administration By Injection

Compound 1 (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

The following formulations illustrate representative pharmaceutical compositions of the present invention.

Formulation Example A

A frozen solution suitable for preparing an injectable solution is prepared as follows:

| Ingredients | Amount |
| --- | --- |
| Active Compound 1 or 1' | 10 to 1000 mg |
| Excipients (e.g., dextrose) | 0 to 50 g |
| Water for Injection Solution | 10 to 100 mL |

Representative Procedure: The excipients, if any, are dissolved in about 80% of the water for injection and the active Compound 1 or 1' is added and dissolved. The pH is adjusted with 1 M sodium hydroxide to 3 to 4.5 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

Formulation Example B

A lyophilized powder or crystalline solid suitable for preparing an injectable solution is prepared as follows:

| Ingredients | Amount |
| --- | --- |
| Active Compound 1 or 1' | 10 to 1000 mg |
| Excipients (e.g., mannitol and/or sucrose) | 0 to 50 g |
| Buffer Agent (e.g., citrate) | 0 to 500 mg |
| Water for Injection | 10 to 100 mL |

Representative Procedure: The excipients and/or buffering agents, if any, are dissolved in about 60% of the water for injection. The active Compound 1 or 1' is added and dissolved and the pH is adjusted with 1 M sodium hydroxide to 3 to 4.5 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored under refrigeration.

Formulation Example C

An injectable solution for intravenous administration to a patient is prepared from Formulation Example B above as follows:
Representative Procedure: The lyophilized powder of Formulation Example B (e.g., containing 10 to 1000 mg of active Compound 1 or 1') is reconstituted with 20 mL of sterile water and the resulting solution is further diluted with 80 mL of sterile saline in a 100 mL infusion bag. The diluted solution is then administered to the patient intravenously over 30 to 120 minutes.

Exemplary Compositions for Administration by Inhalation

Compound 1 (0.2 mg) is micronized and then blended with lactose (25 mg). This blended mixture is then loaded into a gelatin inhalation cartridge. The contents of the cartridge are administered using a dry powder inhaler, for example.
Alternately, micronized Compound 1 (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.
Alternately, Compound 1 (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of Compound 1 per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:
BOC t-butoxycarbonyl (—C(O)OC(CH$_3$)$_3$)
DCM dichloromethane or methylene chloride
DIPEA N,N-diisopropylethylamine
DMF N,N-dimethylformamide
EDTA ethylenediaminetetraacetic acid
EtOH ethanol
Et$_2$O diethyl ether
EtOAc ethyl acetate
HATU N,N,N',N'-tetramethyl-O-(7-azabenzotriazol-1-yl) uronium hexafluorophosphate
KHMDS potassium bis(trimethylsilyl)amide
MeCN acetonitrile
NaHMDS sodium bis(trimethylsilyl)amide
Pd(dppf)$_2$Cl$_2$ 1,1-bis(diphenylphosphino)ferrocene palladium chloride
Pd(PPh$_3$)$_4$ tetrakis(triphenylphosphine)palladium(0)
PE petroleum ether
PyBOP benzotriazol-1-yloxytris(pyrrolidino)phosphonium hexafluorophosphate
TFA trifluoroacetic acid
THF tetrahydrofuran
Unless noted otherwise, all materials, such as reagents, starting materials and solvents, were purchased from commercial suppliers (such as Sigma-Aldrich, Fluka Riedel-de Haën, and the like) and were used without further purification.
Reactions were run under nitrogen atmosphere, unless noted otherwise. The progress of reactions was monitored by thin layer chromatography (TLC), analytical high performance liquid chromatography (anal. HPLC), and mass spectrometry, the details of which are given in specific examples. Generally, solvents used in analytical HPLC were as follows: solvent A was 98% H$_2$O/2% MeCN /1.0 mL/L TFA; solvent B was 90% MeCN/10% H$_2$O/1.0 mL/L TFA.
Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers was done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Measurement Techniques

Powder X-Ray Diffraction

Powder X-ray diffraction analysis was performed using a Bruker D8-Advance X-ray diffractometer. The X-ray source was Cu-Kα radiation with output voltage of 40 kV and current of 40 mA. The instrument was operated in Bragg-Brentano geometry and used Goebel Mirrors to obtain parallel X-ray beam. Any divergence in the beam was limited by a 0.2° vertical divergence slit at the source and Soller slits (2.5°) at the source and the detector. For measurement, a small amount of powder (5-25 mg) was gently pressed onto a zero-background silicon sample-holder to form a smooth surface and subjected to X-ray exposure. The samples were scanned in coupled θ-2θ mode from 2° to 35° in 2θ with a step size of 0.02° and a scan speed of 0.3 seconds per step. The data acquisition was controlled by Bruker DiffracSuite software and analyzed by Jade software (version 7.5.1). The instrument was calibrated with a corundum standard, within ±0.02° 2θ angle.

It should be kept in mind that the Bragg-Brentano geometry used in the data collection is prone to preferred orientation. Under these conditions it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

Differential Scanning Calorimetry

DSC measurements were performed using a TA Instruments Model Q-100 module with a Thermal Analyst controller. Data were collected and analyzed using TA Instruments Universal Analysis software. A sample was accurately weighed into a covered aluminum pan. After a 5 minute isothermal equilibration period at 5° C., the sample was heated using a linear heating ramp of 10° C./min from 0° C. to 200° C.

Thermogravimetric Analysis

Thermal gravimetry measurements were performed using a TA Instruments Model Q-500 module equipped with high resolution capability. Data were collected using TA Instruments Thermal Analyst controller and analyzed using TA Instruments Universal Analysis software. A weighed sample was placed onto a platinum pan and scanned with a heating rate of 10° C./min from ambient temperature to 200° C. The balance and furnace chambers were purged with nitrogen flow during use.

Polarized Light Microscopy

For polarized light microscope (PLM) studies, samples were examined under an optical microscope (Olympus BX51) with cross-polarized light filter. Images were collected with a PaxCam camera controlled by PaxIt Imaging Software (version 6.4). Samples were prepared on glass slides with light mineral oil as immersion medium. Depending on the size of the particles, a 4×, a 10× or a 20× objective lens was used for magnification.

Dynamic Moisture Sorption Assessment

DMS measurements were performed using a VTI atmospheric microbalance, SGA-100 system (VTI Corp., Hialeah, Fla. 33016). A weighed sample was used and the humidity was lowest possible value (close to 0% relative humidity) at the start of the analysis. The DMS analysis consisted of a scan rate of 5% relative humidity/step over the full humidity range of 5-90%. The DMS run was performed isothermally at 25° C.

Synthetic Procedures And Comparative Examples

The following compounds were synthesized and evaluated for NEP enzyme inhibition activity:

| Compound Name | Preparation/ Example | Structure |
| --- | --- | --- |
| Compound 1 | Preparation 1/ Example 1 | 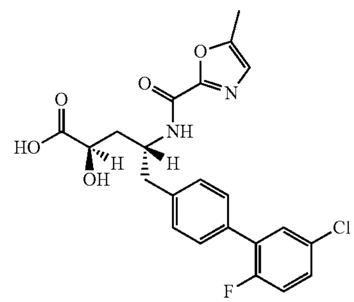 [SMILES: Cc1cnc(C(=O)N[C@H](Cc2ccc(-c3cc(Cl)ccc3F)cc2)C[C@@H](O)C(=O)O)o1] |
| Comparison Compound C2 | Preparation 1/ Example 2 | 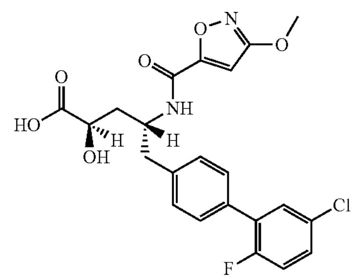 [SMILES: COc1cc(C(=O)N[C@H](Cc2ccc(-c3cc(Cl)ccc3F)cc2)C[C@@H](O)C(=O)O)on1] |
| Comparison Compound C3 | Preparation 2/ Example 3 | 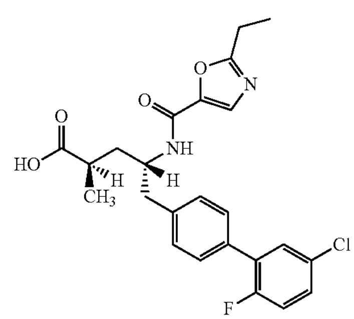 [SMILES: CCc1ncc(C(=O)N[C@H](Cc2ccc(-c3cc(Cl)ccc3F)cc2)C[C@@H](C)C(=O)O)o1] |
| Comparison Compound C4 | Preparation 2/ Example 4 | 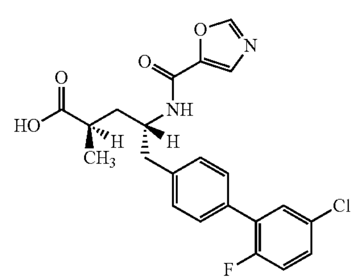 [SMILES: C[C@H](C[C@@H](Cc1ccc(-c2cc(Cl)ccc2F)cc1)NC(=O)c1cnco1)C(=O)O] |

Preparation 1

(2R,4R)-4-Amino-5-(5'-chloro-2'-fluorobiphenyl-4-yl)-2-hydroxypentanoic Acid Ethyl Ester (Compound 7)

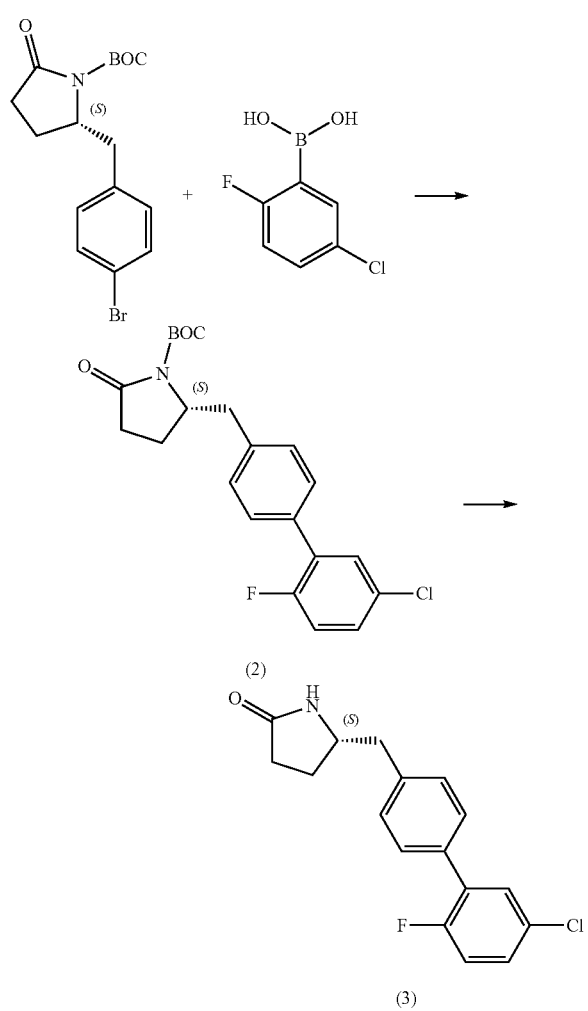

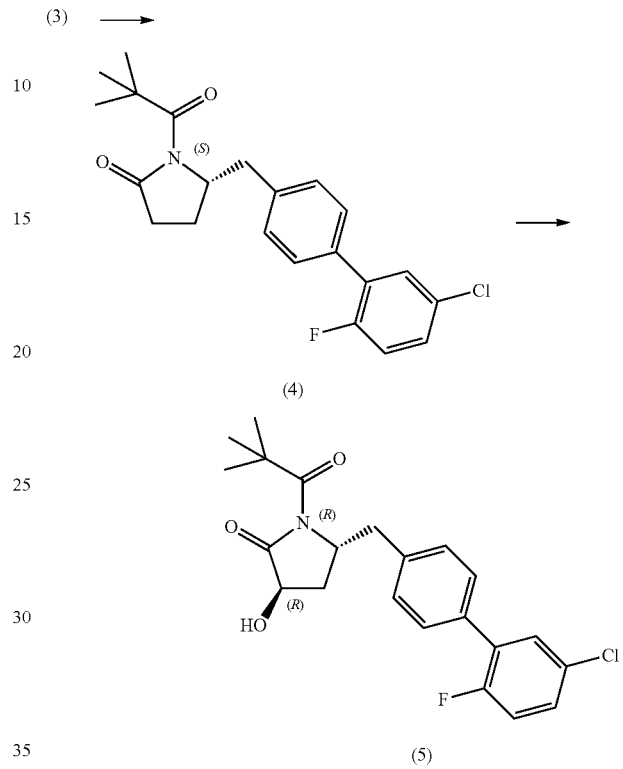

To a solution of (S)-2-(4-bromobenzyl)-5-oxopyrrolidine-1-carboxylic acid t-butyl ester (25 g, 70.6 mmol) in 1,4-dioxane (500 mL) was added 5-chloro-2-fluorophenylboronic acid (24.6 g, 141 mmol), Pd(PPh$_3$)$_4$ (4.1 g, 3.5 mmol) and a solution of K$_2$CO$_3$ (17.8 g, 141 mmol) in water (90 mL), at room temperature under nitrogen. The mixture was heated to 60° C. and stirred overnight. Water (500 mL) was added and the solvent evaporated. The mixture was extracted with EtOAc (200 mL×3). The combined organic layers were washed with saturated aqueous NaCl (300 mL) and filtered. The filtrate was concentrated to yield the crude residue which was purified by chromatography to yield Compound 2 (22.7 g) as a light yellow solid. LC-MS: 829.2 [2M+Na$^+$].

To a solution of Compound 2 (4.9 g, 12.1 mol) in DCM (100 mL) was added TFA (4.5 mL, 60.7 mmol) at 0° C. under nitrogen, and stirred for 1 hour. The mixture was warmed to room temperature for 1.5 hours. After evaporation of the solvent, the residue was diluted with EtOAc (100 mL), then washed with saturated aqueous NaHCO$_3$ (100 mL×3), water (100 mL×2), saturated aqueous NaCl (100 mL), and then dried over Na$_2$SO$_4$. The mixture was filtered and the filtrate was concentrated to yield crude Compound 3. LC-MS: 304 [M+H]$^+$.

To a solution of NaH (2.4 g, 695 mmol) in THF (200 mL) was added dropwise a solution of Compound 3 (8.5 g, 278 mmol) in THF (50 mL) at 0° C. under nitrogen. The mixture was warmed to room temperature and stirred for 2 hours. After cooling to 0° C., pivaloyl chloride (5 g, 41.7 mmol) was added dropwise over 30 minutes. The mixture was warmed to room temperature and stirred for 9.5 hours. The reaction was quenched with saturated aqueous NH$_4$Cl (250 mL) and extracted with EtOAc (400 mL×3). The combined organic layers were dried over Na$_2$SO$_4$ and concentrated to yield the crude residue which was purified by chromatography to yield Compound 4 (18 g) as a yellow solid. LC-MS: 388 [M+H$^+$].

To a solution of Compound 4 (9 g, 23.2 mmol) in THF (200 mL) was added dropwise NaHMDS (20.9 mL, 41.8 mmol) at −78° C. under nitrogen. After stirring for 1 hour at −78° C., a solution of (+)-(8,8-dichlorocamphorylsulfonyl)oxaziridine (10.4 g, 34.8 mmol) in THF (50 mL) was added dropwise. After stirring at −78° C. for 1 hour, the reaction was quenched with saturated aqueous NH$_4$Cl (50 mL) and extracted with EtOAc (400 mL×3). The combined organic layers were washed with 1M aqueous HCl (400 mL), saturated aqueous NaHCO$_3$ (400 mL), and saturated aqueous NaCl (400 mL), dried over Na$_2$SO$_4$, and concentrated to give the crude residue which was purified by chromatography to yield Compound 5 (8.8 g) as a white semi-solid. LC-MS: 426.1 [M+Na$^+$].

(5) → 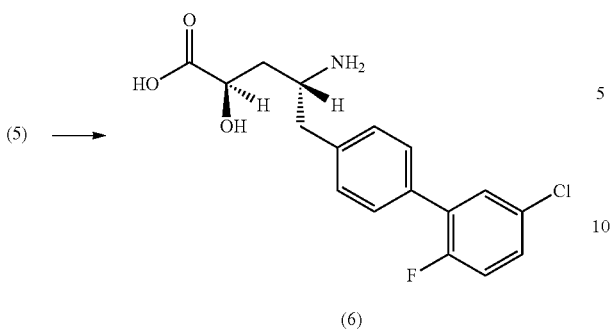

(6)

A solution of Compound 5 (8.8 g, 21.8 mmol) in EtOH (12 mL) was added to concentrated HCl (200 mL) and heated at 100° C. and stirred overnight. The mixture was then concentrated to give the crude residue which was purified by washing with Et₂O (100 mL) to yield Compound 6 (7.5 g) as a solid HCl salt. LC-MS: 338 [M+H⁺].

(6) → 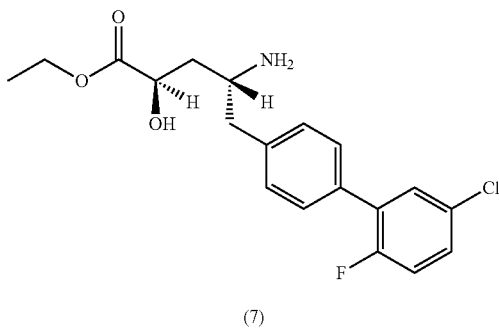

(7)

A solution of Compound 6 (7.5 g, 20.1 mmol) in 1:1 EtOH/HCl (100 mL) was heated at 50° C. overnight. The mixture was concentrated and the crude residue was purified by washing with Et₂O (200 mL) to yield Compound 7 (6.5 g) as a white solid HCl salt. LC-MS: 366.1 [M+H⁺].

Example 1

(2R,4R)-5-(5'-Chloro-2'-fluorobiphenyl-4-yl)-2-hydroxy-4-[(5-methyloxazole-2-carbonyl)amino]pentanoic Acid (Compound 1)

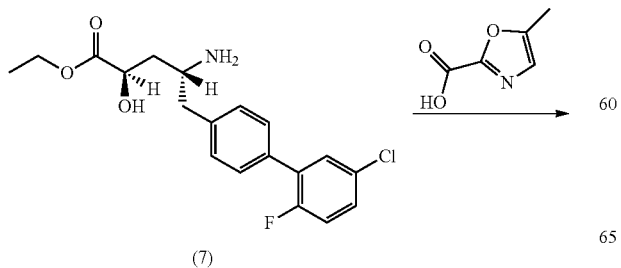

(7)

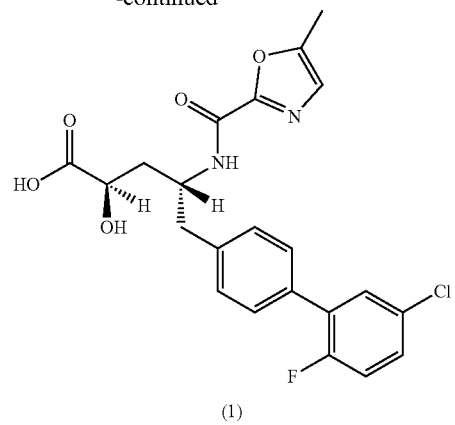

(1)

5-Methyloxazole-2-carboxylic acid (182 mg, 1.4 mmol) and HATU (546 mg, 1.4 mmol) were combined with DMF (3 mL) and stirred for 15 minutes at room temperature. Compound 7 (500 mg, 1.4 mmol) and DIPEA (716 µL, 4.1 mmol) were then added. The resulting mixture was stirred for 15 minutes at room temperature, at which point LC/MS showed completion. The solvent was removed in vacuo and the crude residue was purified by normal flash chromatography (hexanes:EtOAC 20-95%) to yield a solid (590 mg, 1.2 mmol), which was dissolved in dry EtOH (5 mL) and dry THF (5 mL). A solution of 1N LiOH in water (9.9 mL, 9.9 mmol) was then added. The resulting solution was stirred at room temperature for 1 hour, at which point LC/MS showed completion. The solvent was removed in vacuo and the crude residue was purified by reverse phase chromatography to yield Compound 1 (490 mg) as a white powder. MS m/z [M+H]⁺ calc'd for $C_{22}H_{20}ClFN_2O_5$, 447.10; found 447.2.

Crystalline Non-solvated (2R,4R)-5-(5'-Chloro-2'-fluorobiphenyl-4-yl)-2-hydroxy-4-[(5-methyloxazole-2-carbonyl)amino]pentanoic Acid (Compound 1')

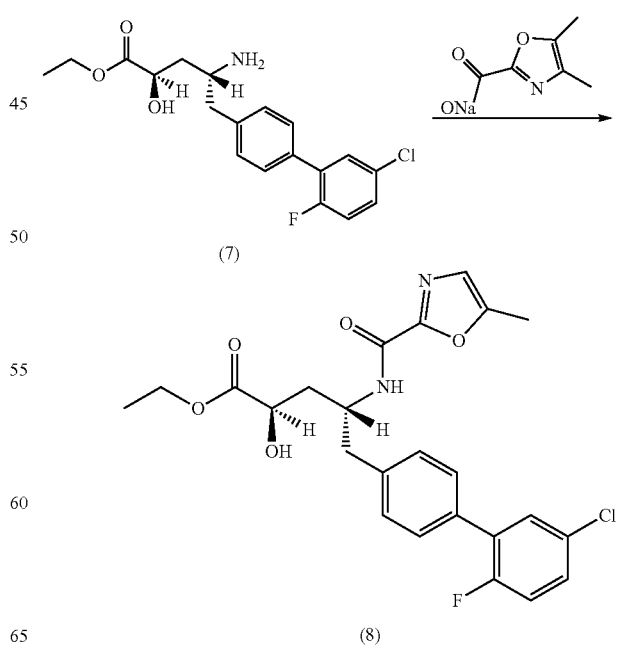

(7)

(8)

Compound 7 (HCl; 190.0 g, 472 mmol) was dissolved in DMF (2 L) and the resulting mixture was cooled to 0° C. Sodium 5-methyloxazole-2-carboxylate (73.9 g, 496 mmol) was added, followed by DIPEA (124 mL, 708 mmol) was added in one portion. PyBOP (320 g, 614 mmol) was added in portions over 20 minutes, while maintaining the internal temperature below 10° C. (6.5° C. max), and the resulting mixture was stirred at 0° C. for 1 hour and then at 20° C. for 1 hour, while monitoring the reaction. At >99% conversion, the mixture was then stirred for an additional 30 minutes at room temperature. EtOAc (6 L) and water (5 L) were added and the resulting mixture was stirred for 20 minutes. The phases were separated and the organic layer was washed with 0.5M HCl (5 L), a 5% aqueous NaHCO₃ solution (5 L) and a 5% saturated aqueous NaCl solution (5 L). The organic layer was dried over Na₂SO₄ for 24 hours at room temperature, then concentrated by rotary evaporation. THF (500 mL) was added and the resulting mixture was concentrated to yield Compound 8 as a thick oil.

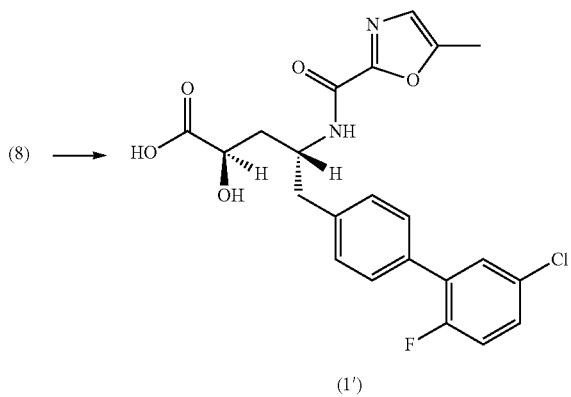 [SMILES: Cc1cnc(C(=O)N[C@H](Cc2ccc(-c3cc(Cl)ccc3F)cc2)C[C@@H](O)C(=O)O)o1]

Crude Compound 8 (224 g, 472 mmol) was dissolved in THF (2 L). LiOH monohydrate (39.6 g, 944 mmol) dissolved in water (400 mL) was added and resulting mixture was stirred at room temperature, while monitoring the reaction. Complete conversion was observed after 2 hours. The reaction was then quenched with 1M aqueous HCl (1180 mL, 1180 mmol). EtOAc (2 L) and saturated aqueous NaCl (2 L) were added and the resulting mixture was stirred for 15 minutes. The phases were separated and the organic layer was washed with a 10% aqueous NaCl solution (3 L) and dried over Na₂SO₄ (500 g) overnight, followed by solvent removal. To the resulting oil was added EtOAc (2 L) and the volume was reduced to about 500 mL. The resulting slurry was stirred at room temperature for 30 minutes, yielding a thick hard to stir slurry (developed in 10 minutes). Hexanes (500 mL) were added slowly (over 10 minutes) and the resulting free-flowing slurry was stirred for 20 minutes at room temperature. Filtration and drying yielded Compound 1' (170 g; 99.2% pure material) as a solid. This product was analyzed by PXRD, DSC, and thermal gravimetry, as described herein, and was determined to be a non-solvated crystalline material. This data is presented in FIGS. 1-3.

Example 2

(2R, 4R)-5-(5'-Chloro-2'-fluorobiphenyl-4-yl)-2-hydroxy-4-[(3-methoxyisoxazole-5-carbonyl)amino]pentanoic Acid (Comparison Compound C2)

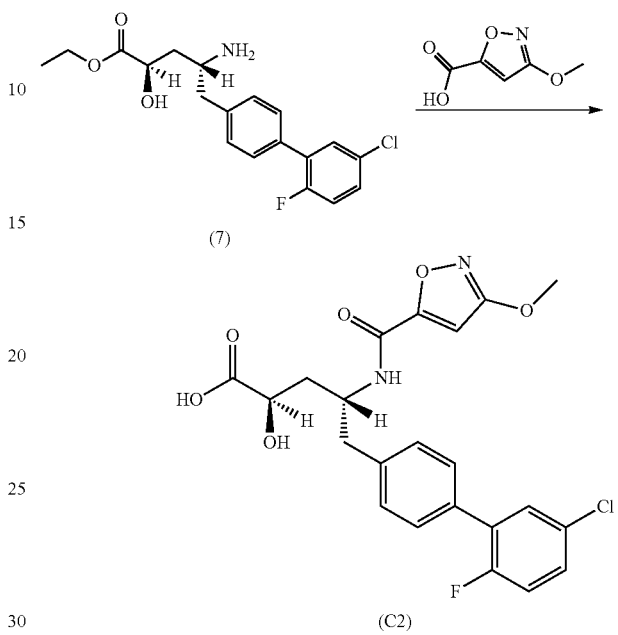

DIPEA (227 μL, 1.3 mmol) was added to a solution of 3-methoxyisoxazole-5-carboxylic acid (74.7 mg, 522 μmol), Compound 7 (175 mg, 435 μmol) and HATU (248 mg, 653 μmol) in DMF (2 mL). The resulting mixture was stirred for 10 minutes at room temperature, at which point LC/MS showed completion. 5.0 M aqueous LiOH (696 μL, 3.5 mmol) was added and the mixture was stirred at room temperature for 30 minutes. Concentrated HCl (~0.4 mL) was added until the reaction mixture became acidic, and the crude mixture was purified by reverse phase chromatography (30-90% MeCN in water with 0.05% TFA) to yield Comparison Compound C2 (132 mg) as a white solid. MS m/z [M+H]⁺ calc'd for $C_{22}H_{20}ClFN_2O_6$, 463.10; found 463.2.

Comparison Compound C2 is described in example 19-9 of U.S. Pat. No. 8,586,536 to Gendron et al.

Preparation 2

(2R,4S)-4-Amino-5-(5'-chloro-2'-fluorobiphenyl-4-yl)-2-methylpentanoic Acid Ethyl Ester (Compound 11)

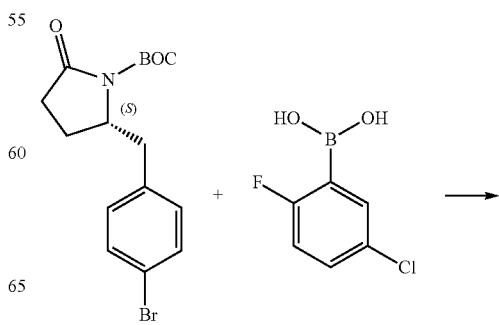

43

-continued

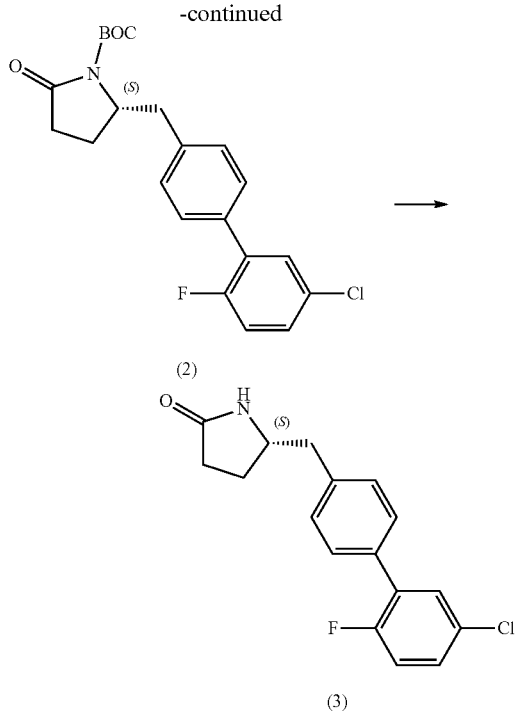

(S)-2-(4-bromobenzyl)-5-oxopyrrolidine-1-carboxylic acid t-butyl ester (90 g, 254 mmol), 5-chloro-2-fluorophenylboronic acid (48.7 g, 279.4 mmol), Pd(dppf)$_2$Cl$_2$ (5.6 g, 7.6 mmol), KF (29.5 g, 508 mmol) in dioxane (900 mL) and water (300 mL), were combined at room temperature under nitrogen. The resulting solution was heated to 85° C. and stirred for 4 hours. Water (500 mL) was added, and the mixture was extracted with EtOAc (500 mL×2). The combined organic layers were washed with saturated aqueous NaCl (500 mL), dried, concentrated and purified by chromatography (PE/EtOAc=6:1 to 3:1) to yield Compound 2 (96 g) as yellow solid. LC-MS: m/z=348[(M−56)$^+$+1].

To a solution of Compound 2 (20 g, 49.5 mmol) in anhydrous DCM (200 mL) was added TFA (30 mL) at 0° C. under nitrogen. The mixture was warmed to room temperature and stirred at room temperature for 2 hours. After evaporation of the solvent, the residue was diluted with EtOAc (200 mL), then washed with saturated aqueous NaHCO$_3$ (200 mL×3) and saturated aqueous NaCl (200 mL×2). The organic layer was dried and concentrated to yield Compound 3 (14 g, crude) as a yellow oil. LC-MS: m/z=304[(M$^+$+1)], m/z=607[(2M$^+$+1)].

(3) →

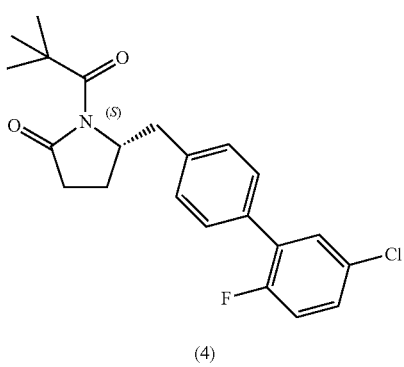

44

-continued

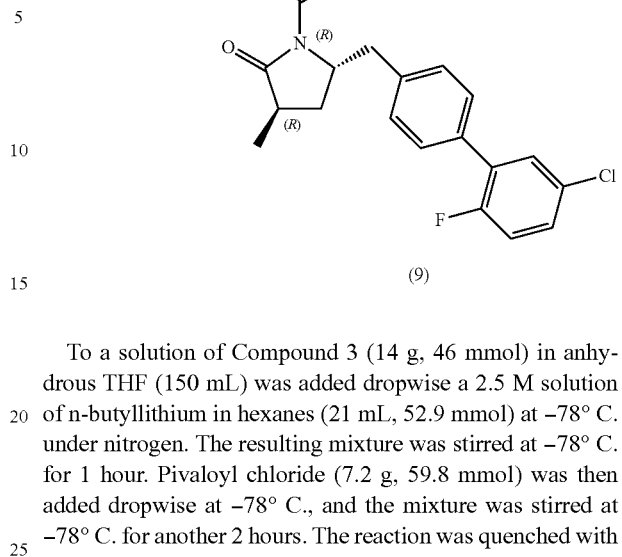

To a solution of Compound 3 (14 g, 46 mmol) in anhydrous THF (150 mL) was added dropwise a 2.5 M solution of n-butyllithium in hexanes (21 mL, 52.9 mmol) at −78° C. under nitrogen. The resulting mixture was stirred at −78° C. for 1 hour. Pivaloyl chloride (7.2 g, 59.8 mmol) was then added dropwise at −78° C., and the mixture was stirred at −78° C. for another 2 hours. The reaction was quenched with water (200 mL) and extracted with EtOAc (200 mL×2). The combined organic layers were washed with saturated aqueous NaCl (200 mL), dried over Na$_2$SO$_4$, concentrated, and purified by column chromatography (PE/EtOAc=50:1) to yield Compound 4 (14.6 g) as a light yellow oil. LC-MS: m/z=388[(M$^+$+1)].

To a solution of Compound 4 (14.6 g, 37.4 mmol) in toluene (200 mL) was added dropwise KHMDS (82 mL, 41.1 mmol) at −78° C. under nitrogen. After stirring at −78° C. for 2 hours, Me$_2$SO$_4$ (4.3 mL, 44.9 mmol) was added dropwise. After stirring at −78° C. for 2 hours, the reaction was quenched with saturated aqueous NH$_4$Cl (100 mL) and extracted with EtOAc (100 mL×2). The combined organic layers were washed with saturated aqueous NaCl (200 mL), dried over Na$_2$SO$_4$, filtered, and concentrated to give the crude product which was purified by chromatography (PE/EtOAc=100:1) to yield Compound 9 (3.4 g) as a colorless oil. LC-MS: m/z=402[(M$^+$+1)].

(9) →

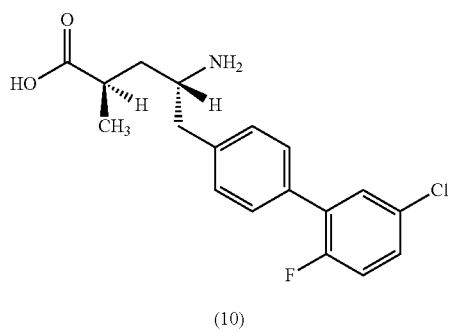

A solution of Compound 9 (3.4 g, 8.5 mmol) in concentrated HCl (50 mL) was refluxed for 2 days. The mixture was then concentrated under reduced pressure and the residue was purified by washing with EtOAc (20 mL) to yield Compound 10 (2.2 g) as an off white solid HCl salt. LC-MS: m/z=336[(M$^+$+1)].

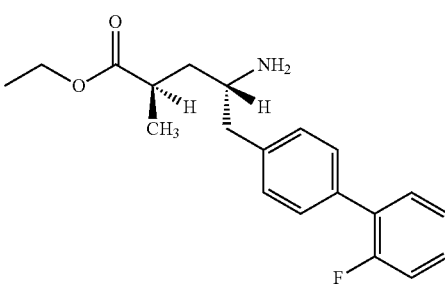

A solution of Compound 10 (2.2 g, 5.9 mmol) in 4 M HCl in EtOH (15 mL) was stirred at room temperature for 2 hours. The mixture was then concentrated under reduced pressure and the residue was purified by washing with EtOAc (20 mL) to yield Compound 11 (2.3 g) as an off white solid. LC-MS: m/z=364[(M$^+$+1)] $^1$H NMR (300 MHz, DMSO) δ 7.61-7.52 (m, 3H), 7.47 (ddd, J=8.7, 4.3, 2.7 Hz, 1H), 7.38 (dd, J=13.5, 5.5 Hz, 3H), 3.98 (q, J=7.1 Hz, 2H), 3.37 (d, J=11.1 Hz, 1H), 3.11 (dd, J=13.7, 5.1 Hz, 1H), 2.90-2.67 (m, 2H), 1.85 (ddd, J=14.0, 9.3, 4.8 Hz, 1H), 1.68-1.54 (m, 1H), 1.13-0.99 (m, 6H).

Example 3

(2R,4S)-5-(5'-Chloro-2'-fluorobiphenyl-4-yl)-4-[(2-ethyloxazole-5-carbonyl)amino]-2-methylpentanoic Acid (Comparison Compound C3)

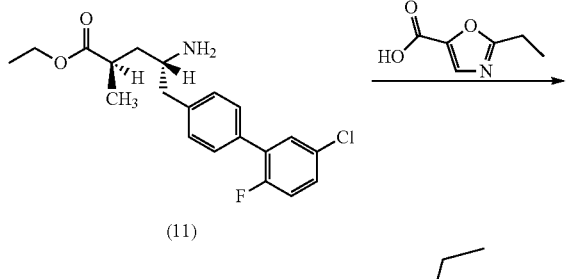

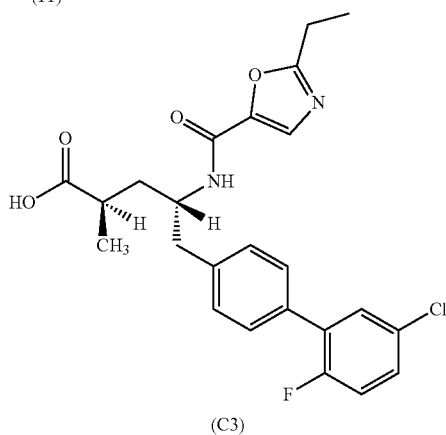

DIPEA (228 μL, 1.3 mmol) was added to a solution of 2-ethyloxazole-5-carboxylic acid (67.9 mg, 481 μmol), Compound 11 (175 mg, 437 μmol), and HATU (249 mg, 656 μmol) in DMF (2.0 mL), and stirred at room temperature for 15 minutes. 5.0 M Aqueous LiOH (699 μL, 3.5 mmol) was added and the mixture was stirred at room temperature for 1.5 hours. Concentrated HCl (~0.5 mL) was added until the mixture became acidic and the crude mixture was purified by preparatory HPLC (20-80% MeCN in water with 0.05% TFA) to yield Comparison Compound C3 (170 mg) as a white solid. MS m/z [M+H]$^+$ calc'd for $C_{24}H_{24}ClFN_2O_4$, 459.14; found 459.05.

Comparison Compound C3 is described in example 71-1 of. U.S. Pat. No. 8,263,629 to Coppola et al.

Example 4

(2R,4S)-5-(5'-Chloro-2'-fluorobiphenyl-4-yl)-2-methyl-4-[(oxazole-5-carbonyl)amino]pentanoic Acid (Comparison Compound C4)

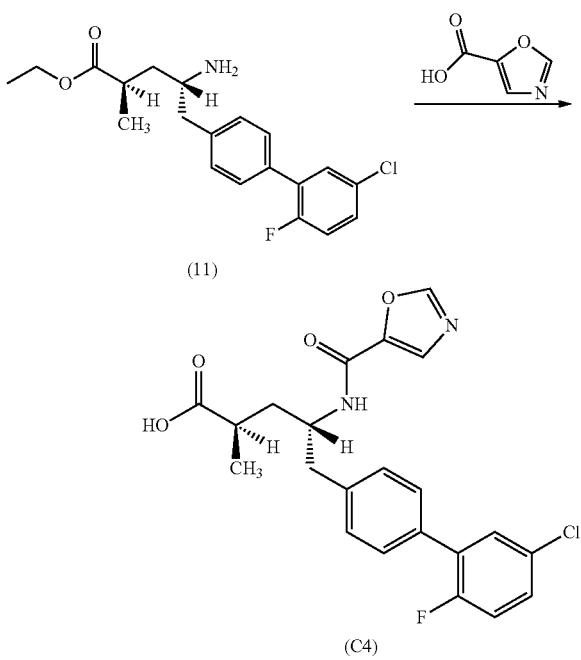

DIPEA (228 μL, 1.3 mmol) was added to a solution of oxazole-5-carboxylic acid (49.4 mg, 437 μmol), Compound 11 (HCl; 175 mg, 437 μmmol) and HATU (249 mg, 656 μmmol) in DMF (2 mL). The resulting mixture was stirred for 10 minutes at room temperature, at which point LC/MS showed completion. 5.0 M aqueous LiOH (699 μL, 3.5 mmol) was added and the mixture was stirred at room temperature for 1 hour. Concentrated HCl (~0.5 mL) was added until the reaction mixture became acidic and the crude mixture was purified by preparative HPLC (20-80% MeCN in water with 0.05% TFA) to yield Comparison Compound C4 (103 mg) as a white solid. MS m/z [M+H]$^+$ calc'd for $C_{22}H_{20}ClFN_2O_4$, 431.11; found 431.1.

Comparison Compound C4 is described in example 68-1 of. U.S. Pat. No. 8,263,629 to Coppola et al.

Assays

Compound 1 and Comparison Compounds C2, C3 and C4 were evaluated in the assays described below.

Assay 1

In vitro Assay for the Quantitation of Inhibitor Potency at Human NEP

The inhibitory activity at human neprilysin (EC 3.4.24.11; NEP) was determined as follows.

Recombinant human NEP was obtained commercially (R&D Systems, Minneapolis, Minn., catalog number 1182-ZN). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) was used.

The assay was performed in 384-well white opaque plates at 37° C. using the fluorogenic peptide substrate at a concentration of 10 µM in Assay Buffer (50 mM HEPES, pH 7.5, 100 mM NaCl, 0.01% polyethylene glycol sorbitan monolaurate (Tween-20), 10 µM $ZnSO_4$). The enzyme was used at a concentration that resulted in quantitative proteolysis of 1 µM of substrate after 20 minutes at 37° C.

Test compounds were assayed over the range of concentrations from 10 µM to 20 µM. Test compounds were added to the enzyme and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm. Inhibition constants were obtained by nonlinear regression of the data using the equation (GraphPad Software, Inc., San Diego, Calif.):

$$v = v_0 / [1 + (I/K')]$$

where $v$ is the reaction rate, $v_0$ is the uninhibited reaction rate, $I$ is the inhibitor concentration and $K'$ is the apparent inhibition constant.

The compounds were tested in this assay and found to have $pK_i$ values at human NEP as follows.

| Compound | $pK_i$ |
|---|---|
| 1 | 9.7 |
| C2 | 9.9 |
| C3 | 9.1 |
| C4 | 9.3 |

Assay 2

IV/PO Pharmacokinetic Study in Rats and Dogs

Each rat or dog PK study began with formulation of the test compound. Appropriate masses of each test compound were added into a volume of vehicle (e.g. 5% sodium bicarbonate, 5% dextrose in $H_2O$) such that the final concentration of each compound was appropriate to be dosed at 2 mL/kg. Although a homogenous suspension were acceptable for oral dosing, intravenous dosing solutions were sterile-filtered (0.2 µm) prior to dosing to ensure no particulates were administered.

In the rat study, pre-cannulated male Sprague-Dawley rats (3 per route) between 8 and 10 weeks of age were obtained from Harlan Laboratories (Indianapolis, Ind.). Rats received either a single oral gavage or a single intravenous (via lateral tail vein) dose of the dosing solution. The final dose was typically 0.5-3 mg/kg. Serial blood samples were harvested via the cannula implanted in the jugular vein at 3 minutes, 15 minutes, 30 minutes, 1 hour, 2 hours, 4 hours, 6 hours, and 24 hours post-dose. Sampling was performed either manually or using automated blood samplers. Samples were collected into microtainer tubes containing EDTA as the anticoagulant and were processed to plasma by refrigerated centrifugation.

In the dog study, male beagle dogs (3 per route) housed at Agilux Laboratories (Worcester, Mass.) and weighing between 7-12 kg received either a single oral gavage or a single intravenous (via indwelling catheter) dose of the dosing solution. The final dose was typically 0.1-2 mg/kg. Serial blood samples were harvested via direct venipuncture at 3 minutes, 15 minutes, 30 minutes, 1 hour, 2 hours, 4 hours, 6 hours, 8 hours, 12 hours, and 24 hours post-dose. All samples were collected manually into microtainer tubes containing EDTA as the anticoagulant and were processed to plasma by refrigerated centrifugation.

Plasma samples were extracted with 3 volumes of MeCN containing a suitable internal standard. Extracts were reconstituted into 3 volumes of water containing 1% formic acid, and analyzed via HPLC-coupled MS/MS. Plasma concentration-time data were analyzed using the Phoenix software (Pharsight Corp., St. Louis, Mo.) to calculate pharmacokinetic parameters.

Plasma clearance was determined from the intravenous arm of the study, and represents the rate at which plasma is cleared of drug. It is equal to the dose divided by the area under the plasma concentration-time curve. In addition to plasma clearance, it is also essential for an orally administered drug to reach efficacious systemic levels following oral delivery. Oral bioavailability is a measurement of plasma exposures following oral administration relative to exposures following intravenous administration.

Rat Pharmacokinetic Data

| Compound Dosed | Route | $AUC_{last}$[a] (µg*hr/mL) Mean | $CL_{last}$[b] (L/hr/kg) Mean | Oral Bioavailability (%)[c] Mean |
|---|---|---|---|---|
| 1 | IV | 0.61 | 0.83 | — |
|  | PO | 0.40 | — | 67% |
| C2 | IV | 0.48 | 1.7 | — |
|  | PO | 0.11 | — | 20% |
| C3 | IV | 1.5 | 0.60 | — |
|  | PO | 0.88 | — | 60% |
| C4 | IV | 0.83 | 0.67 | — |
|  | PO | 0.50 | — | 60% |

[a] $AUC_{last}$ is the area under the plasma concentration versus time curve from time 0 to the time after dosing at which the last quantifiable concentration was observed, estimated by linear trapezoidal method
[b] $CL_{last}$ is the dose divided by $AUC_{last}$
[c] Oral Bioavailability is calculated as $AUC_{last}$ following oral administration, divided by $AUC_{last}$ following intravenous administration, normalized for any differences in administered doses, expressed as a percentage This rat data shows that the compound of the invention (Compound 1) has high oral bioavailability (67%). The comparison Compounds C3 and C4 exhibited similar oral bioavailability (60% and 60%, respectively). However, comparison Compound C2 had lower oral bioavailability (20%). This rat data also shows that Compound 1 has a similar low clearance rate compared to that of comparison Compounds C3 and C4 (0.83, 0.60, and 0.67, respectively). However, comparison Compound C2 was much more rapidly cleared (mean $CL_{last}$ of 1.7).

In order to obtain a more predictive determination of how a compound will behave in humans (e.g., safety and efficacy), evaluation in a second animal species was performed.

Dog Pharmacokinetic Data

| Compound Dosed | Route | AUC$_{last}$ (μg*hr/mL) Mean | CL$_{last}$ (L/hr/kg) Mean | Oral Bioavailability (%) Mean |
|---|---|---|---|---|
| 1 | IV | 0.51 | 0.29 | — |
|  | PO | 0.53 | — | >100%* |
| C2 | IV | 0.16 | 0.65 | — |
|  | PO | 0.16 | — | 99% |
| C3 | IV | 0.17 | 0.59 | — |
|  | PO | 0.13 | — | 64% |
| C4 | IV | 0.07 | 1.54 | — |
|  | PO | 0.03 | — | 42% |

*Greater than 100% bioavailability may relate to absorption, distribution and or elimination processes.

This dog data shows that the compound of the invention (Compound 1) has high oral bioavailability (>100%) and low plasma clearance. While comparison Compounds C2 exhibited similar oral bioavailability (99%), comparison Compounds C3 and C4 exhibited much lower oral bioavailability (64% and 42%, respectively). Additionally, this dog data also shows that Compound 1 has a lower clearance rate (0.29) compared to that of all three comparison Compounds C2, C3, and C4 (0.65, 0.59, and 1.54, respectively).

In conclusion, Compound 1 consistently exhibited both high oral bioavailability and low plasma clearance in both rat and dog. In contrast, comparison Compound C2 exhibited lower bioavailability in rats than Compound 1 and higher plasma clearance in both rat and dog than Compound 1. Comparison Compounds C3 and C4, while comparable in both oral bioavailability and clearance to Compound 1 in rat, exhibited lower oral bioavailability and high clearance than Compound 1 in dog.

Assay 3

Pharmacokinetic/Pharmacodynamic (PK-PD) assay for NEP Activity in Conscious Normotensive Sprague-Dawley Rats Appropriate masses of each test compound were added into a volume of vehicle (e.g. 5% sodium bicarbonate, 5% dextrose in H$_2$O) such that the final concentration of each compound was appropriate to be dosed at 2 mL/kg. Note that a homogenous suspension was deemed to be acceptable for oral dosing.

Pre-cannulated male Sprague-Dawley rats (3 per compound evaluated) between 8 and 10 weeks of age were obtained from Harlan Laboratories (Indianapolis, Ind.). Rats received a single oral gavage of the dosing solution. The final dose was typically in the range of 3-30 mg/kg. Serial blood samples were harvested via the cannula implanted in the jugular vein at 3 minutes, 15 minutes, 35 minutes, 45 minutes, 1 hour, 2 hours, 4 hours, 6 hours, and 24 hours post-dose. Samples were collected into microtainer tubes containing EDTA as the anticoagulant and were processed to plasma by refrigerated centrifugation. Fifteen minutes prior to the 45 minute, 2 hour, 4 hour, 6 hour, and 24 hour samples, an IV bolus (30 μg/kg) of Atrial Natriuretic Peptide (ANP) was administered. If the test compound successfully inhibited neprilysin, one key mediator of ANP clearance, administered ANP would augment basal levels of ANP, thereby potentiating downstream signaling. If the test compound did not successfully inhibit neprilysin, levels of circulating ANP and the downstream signaling cascade would return to their basal state during the 15 minutes between administration of the ANP bolus and the time point at which the plasma sample was taken. Since binding of ANP to its receptor leads to activation of guanylyl cyclase and subsequent production of cyclic guanosine monophosphate (cGMP), the observation of elevated levels of cGMP (>20 nM) in plasma 15 minutes after the IV administration of the ANP bolus was interpreted as evidence of ongoing neprilysin inhibition. Elevated levels plasma cGMP levels 24 hours after dosing is an indicator of the duration pharmacologic effect, analogous to plasma clearance values as indicators of pharmacokinetic persistence.

Plasma samples were extracted with 3 volumes of MeCN containing a suitable internal standard. Extracts were reconstituted into 3 volumes of water containing 1% formic acid. Plasma cGMP and test compound concentrations were quantified in plasma samples by HPLC-coupled mass spectrometric detection.

| Compound Dosed | Dose (mg/kg) | cGMP Concentration 24 hours After Dosing (nM) Mean$^a$ |
|---|---|---|
| 1 | 3 | 112 |
| C2 | 3 | 45 |
| C3 | 3 | 47 |
| C4 | 3 | 53 |

$^a$Average of three determinations

Thus, the compound of the invention (Compound 1) exhibited more than 2-fold greater potentiation of cGMP 24 hr after dosing as compared to that observed for the prior art Compounds C2, C3, and C4.

Assay 4

IV/PO Pharmacokinetic Study of Compound 1 in Monkeys

A monkey PK study was performed with an appropriate mass of compound 1 in volume of vehicle (e.g., 5% sodium bicarbonate, 5% dextrose in H$_2$O, pH 7.4, for oral and PEG200:EtOH:Water (40:10:50), pH 7.0, filtered through a 0.22 μM PDVF syringe for IV) such that the final concentration was dosed at 0.5 mL/kg (IV) or 2.0 mL/kg (PO).

Male cynomologus monkeys (3 per route) housed at Xenometrics (Stilwell, Kans.) received an IV or PO dose of compound 1 at 1 mg/kg. Animals administered IV doses had access to food ad libitum and those administered PO doses were fasted overnight and received food approximately 4 hours after dose administration. Blood samples were collected from each animal at each time point (pre-dose, 0.083 hour, 0.25 hour, 0.5 hour, 1 hour, 2 hours, 4 hours, 6 hours, 8 hours, 12 hours, and 24 hours) via the cephalic, femoral, or sphenous vein through 48 hours. All samples were collected into K$_2$EDTA tubes and placed on ice. Samples were processed to plasma by centrifugation (3200 rpm, 10 minutes, 5° C.), and acidified with a final concentration of 2% acetic acid. Aliquots of plasma were transferred to a 96-well plate tubes and stored frozen (−70° C.) prior to bioanalysis. Plasma concentrations of compound 1 were determined by LC/MS/MS. Plasma study samples were vortexed and placed in a 96-well plate. The samples were extracted with 200 μL of 0.2% formic acid in acetonitrile with an internal standard. The extract was centrifuged for 10 minutes at 3700 RPM and supernatant was mixed with 0.2% formic acid in water. Samples (15 μL) were injected on a Thermo (C18 50×2.1mm) column with a flow rate of 0.3 mL/min. Mobile phase A consisted of 0.2% formic acid in water and mobile phase B consisted of 0.2% formic acid in acetonitrile. The gradient elution started with 0% to 95% B from 0.5 to 1.5 min., held at 95% from 1.5 to 1.85 min., followed by a gradient of 95% to 0% B from 1.85 to 1.86 min. and stopped at 2.6 min. Compound 1 assay range was 0.0005 to 5 μg/mL. Pharmacokinetic parameters of compound 1 were determined by non-compartmental analysis (Model 201 and Model 200 for IV and PO administration, respectively) using Phoenix WinNonlin Version 6.3 (Certara, Sunnyvale, Calif.) and using individual plasma concentration time profiles from 3 animals.

Plasma clearance was determined from the intravenous arm of the study, and represents the rate at which plasma is cleared of drug. It is equal to the dose divided by the area under the plasma concentration-time curve. In addition to plasma clearance, it is also essential for an orally administered drug to reach efficacious systemic levels following oral delivery. Oral bioavailability is a measurement of plasma exposures following oral administration relative to exposures following intravenous administration.

Monkey Pharmacokinetic Data

| Compound Dosed | Route | $AUC_{last}$ (μg*hr/mL) Mean | $CL_{last}$ (L/hr/kg) Mean | Oral Bioavailability (%) Mean |
|---|---|---|---|---|
| 1 | IV | 2.78 | 0.36 | — |
|   | PO | 1.66 | — | 60% |

This data shows that the compound of the invention (Compound 1) has high oral bioavailability (approximately 60%) and low plasma clearance (approximately 0.36) in male cynomolgus monkeys. This was consistent with and similar to bioavailability and clearance data generated from rat and dog species.

Assay 5

Renal Excretion of Compound 1 in Rat, Dog and Monkey Species

An important factor for insuring appropriate long term drug dosing and correct steady-state drug concentrations in patients is drug clearance. In general, decreased drug clearance results in higher drug concentrations and greater drug effects. In order to understand renal clearance of Compound 1, the percent of administered dose recovered in urine following a single IV dose was assessed in three animal species. Three separate studies in male Sprague Dawley rats, male beagle dogs and male cynomolgus monkeys, respectively, were conducted and the procedure and experimental results are described below.

Male Sprague Dawley rats (N=3), having body weights of 0.348 to 0.362 kg, received an IV dose of Compound 1 at 0.5 mg/kg as part of a dosing cassette. Compound 1 was dissolved in 5% $NaHCO_3$ in D5W (5% dextrose in water, pH 7.4) and filtered through a 0.22 μM polyvinyl difluoride (PVDF) syringe filter prior to administration. The rats had access to food ad libitum before and after administration of Compound 1. Urine samples were collected in metabolic cages and maintained on frozen dry ice during collection. The samples were thawed and the volume of the urine was recorded. An aliquot of the urine sample was transferred to a polypropylene storage tube, frozen and stored (−80° C.) prior to bioanalysis.

Rat urine concentrations of Compound 1 were determined by LC/MS/MS. Urine samples were thawed and diluted 5-fold in rat $K_2EDTA$ plasma. A 50 μL aliquot of the diluted urine was transferred to a 96-well plate and extracted with a 200 μL volume of 2% formic acid in acetonitrile containing an internal standard. The 96-well plate was centrifuged for 10 minutes at 3700 RPM and the supernatant transferred to a new 96-well plate. The supernatant was diluted in 0.2% formic acid in water (4-fold dilution). A 10 or 20 μL volume was injected onto a Xbridge phenyl (21×50mm; 5 μ) column. Mobile phase A consisted of 0.2%formic acid in water and mobile phase B consisted of 0.2% formic acid in acetonitrile. The gradient elution started with 20% to 95% B from 0.5 to 2.0 min, held at 95% from 2.0 to 2.2 min., followed by a gradient of 95% to 20% B from 2.2 to 2.3 min. and stopped at 3.3 min. Compound 1 assay range was 0.00125 to 25 μg/mL.

Male beagle dogs (N=6, two groups of 3), having body weights of 9.04-10.2 kg and 10.8-11.5 kg, received an IV dose of Compound 1 at 0.1 mg/kg (Group I) and 1.255 mg/kg (Group II) as part of a dosing cassette. Compound 1 was dissolved in PEG-200:ethanol:water (40:10:50) and filtered through a 0.22 mM polyvinyl difluoride (PVDF) syringe filter prior to administration. The dogs had access to food ad libitum before and after administration of Compound 1. Urine samples were collected on cold packs into pre-weighed containers that were prefilled with 0.5 mL glacial acetic acid. The samples were weighed again and additional glacial acetic acid was added if needed to a final concentration of 2%. The samples were frozen and stored (−80° C.) prior to bioanalysis.

Dog urine concentrations of Compound 1 were determined by LC/MS/MS. Urine study samples (diluted in plasma $K_2EDTA$(1:9)) were vortexed and 25 μL was placed in a 96-well plate. The samples were extracted with 100 μL in acetonitrile with internal standard Glyburide. The extract was centrifuged for 5 minutes at 3100 RPM and 75 μL of supernatant was transferred and mixed with 150 μL water. Samples (12 μL) were injected on a Waters Acquity UPLC BEH C18 (50×2.1 mm, 1.7 μm) column with a flow rate of 0.9 mL/min. Mobile phase A consisted of 95:5:0.1 (v:v:v) water:acetonitrile:formic acid and mobile phase B consisted of 50:50:0.1 (v:v:v) methanol:acetonitrile:formic acid. The gradient elution started with 35% to 90% B from 0.2 to1.6 min, held at 95% from 1.7 to 2.2 min., followed by a step of 95% to 35% B from 2.20 to 2.30 min. Compound 1 assay range was 0.000100 to 1.00 μg/mL.

Male cynomolgus monkeys (N=3), having body weights of 4.42-5.81 kg, received an IV dose of compound 1 at 1 mg/kg. Compound 1 was dissolved in PEG-200:ethanol:water (40:10:50) and filtered through a 0.22 mM polyvinyl difluoride (PVDF) syringe filter prior to administration. The monkeys had access to food ad libitum before and after administration of Compound 1. Urine samples were collected on dry ice during the collection interval periods, the sample volumes were recorded, and the urine acidified with acetic acid to a final concentration of approximately 2% acetic acid. Aliquots were obtained and frozen (−70° C.) prior to bioanalysis.

Monkey urine concentrations of Compound 1 were determined by LC/MS/MS. Urine samples were thawed and diluted in plasma $K_2EDTA$ (1:4). The samples were extracted with 200 μL of 0.2% formic acid in acetonitrile with internal standard. The extract was centrifuged for 10 minutes at 3700 RPM and supernatant was mixed with 0.2% formic acid in water. The samples (15 μL) were injected on a Thermo (C18 50×2.1 mm) column with a flow rate of 0.3 mL/min. Mobile phase A consisted of 0.2% formic acid in water and mobile phase B consisted of 0.2% formic acid in acetonitrile. The gradient elution started with 0% to 95% B from 0.5 to 1.5 min, held at 95% from 1.5 to 1.85 min, followed by a gradient of 95% to 0% B from 1.85 to 1.86 min. and stopped at 2.6 min. Compound 1 assay range was 0.0025 to 25 μg/mL.

The mean amount of urine excreted over a collection period of 24 hrs and the approximate % of administered dose excreted in urine is reported in the table below.

| Species | Amount of IV Administration (mg/kg) | Amount of Compound 1 Excreted in Urine over Collection Period (0-24 hrs) (μg) Mean[a] | Urinary Excretion (approximate % of administered dose excreted in urine) Mean[a] |
|---|---|---|---|
| Rat | 0.5 | 0.0462 | 0.03% |
| Dog | 0.1 and 1.26 | 15.8 and 103 | 0.92 and 1.67% |
| Monkey | 1 | 157 | 3.14% |

[a]Average of three determinations

The renal excretion of Compound 1 in the rat was approximately 0.03% of the administered dose, in the dog was approximately 1 to 1.5% of the administered dose and in the monkey approximately 3% of the administered dose. These data indicate that Compound 1 has low renal excretion in the three species tested.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A method for treating hypertension, the method comprising administering to patient a therapeutically effective amount of a compound of the following structure:

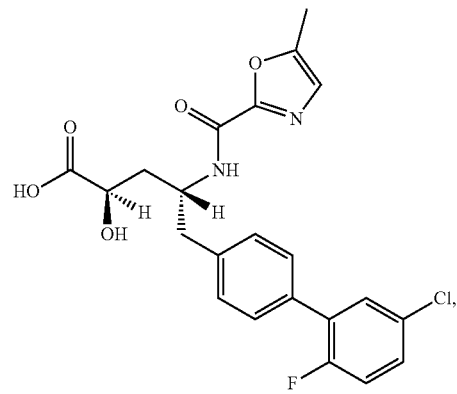

(1)

or a pharmaceutically acceptable salt thereof;
wherein the hypertension is selected from the group consisting of primary hypertension, secondary hypertension, hypertension with accompanying renal disease, severe hypertension with or without accompanying renal disease, pulmonary hypertension, and resistant hypertension.

2. The method according to claim 1, wherein the hypertension is resistant hypertension.

3. A method for treating portal hypertension, the method comprising administering to patient a therapeutically effective amount of a compound of the following structure:

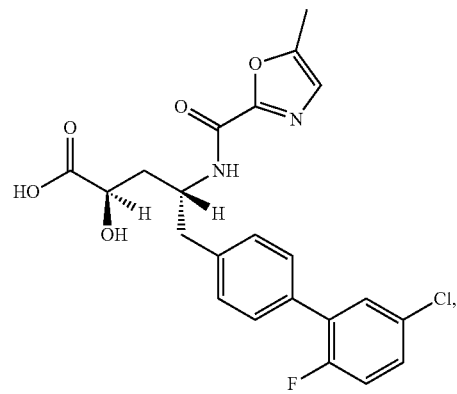

(1)

or a pharmaceutically acceptable salt thereof.

* * * * *